(12) United States Patent
Eim et al.

(10) Patent No.: US 10,350,138 B2
(45) Date of Patent: Jul. 16, 2019

(54) MOBILE TERMINAL, WIRELESS CHARGER AND WEARABLE DEVICE

(71) Applicant: LG Electronics Inc., Seoul (KR)

(72) Inventors: Sanghyun Eim, Seoul (KR); Gukchan Lim, Seoul (KR); Hongjo Shim, Seoul (KR); Jumin Chi, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 895 days.

(21) Appl. No.: 14/827,124

(22) Filed: Aug. 14, 2015

(65) Prior Publication Data

US 2016/0250099 A1    Sep. 1, 2016

(30) Foreign Application Priority Data

Feb. 27, 2015   (KR) .................. 10-2015-0027876

(51) Int. Cl.
| | |
|---|---|
| *A61H 39/04* | (2006.01) |
| *A43B 7/00* | (2006.01) |
| *A43B 7/14* | (2006.01) |
| *A61B 5/00* | (2006.01) |
| *A61B 5/11* | (2006.01) |
| *A61B 5/107* | (2006.01) |

(52) U.S. Cl.
CPC .............. *A61H 39/04* (2013.01); *A43B 7/00* (2013.01); *A43B 7/146* (2013.01); *A61B 5/1077* (2013.01); *A61B 5/1112* (2013.01); *A61B 5/4836* (2013.01); *A61B 5/6812* (2013.01); *A61B 5/6829* (2013.01); *A61H 2201/1261* (2013.01); *A61H 2201/164* (2013.01); *A61H 2201/165* (2013.01); *A61H 2201/5071* (2013.01); *A61H 2205/12* (2013.01); *A61H 2230/805* (2013.01); *A61H 2230/825* (2013.01); *A61H 2230/855* (2013.01)

(58) Field of Classification Search
CPC ......... A43B 7/00; A43B 7/146; A61B 5/1077; A61B 5/1112; A61B 5/4836; A61B 5/6812; A61B 5/6829; A61H 39/04; A61H 2201/1261; A61H 2201/164; A61H 2201/165; A61H 2201/5071; A61H 2205/12; A61H 2230/805; A61H 2230/825; A61H 2230/855
See application file for complete search history.

(56) References Cited

U.S. PATENT DOCUMENTS

| | | | | |
|---|---|---|---|---|
| 5,813,142 | A * | 9/1998 | Demon ................ | A43B 3/0005 36/28 |
| 6,430,843 | B1 * | 8/2002 | Potter ................. | A43B 3/0005 36/28 |

(Continued)

FOREIGN PATENT DOCUMENTS

KR    10-2011-0057726 A    6/2011

*Primary Examiner* — Joshua Lee
(74) *Attorney, Agent, or Firm* — Birch, Stewart, Kolasch & Birch, LLP

(57) ABSTRACT

A wearable mobile terminal is provided that includes a base provided in an insole of a shoe, a pressure sensing unit provided in the base to sense a pressure selectively applied when a user walks, an acupressure unit provided to apply an acupressure to the user's foot, when the pressure is applied to the pressure sensing unit; and a wireless communication unit synchronized with an external mobile terminal.

13 Claims, 31 Drawing Sheets

(56) References Cited

U.S. PATENT DOCUMENTS

| | | | | |
|---|---|---|---|---|
| 6,434,859 B1* | 8/2002 | Kim | A43B 7/142 | 36/43 |
| 7,631,382 B2* | 12/2009 | DiBenedetto | A43B 1/0036 | 12/142 P |
| 7,771,371 B2* | 8/2010 | Avni | G01L 5/008 | 600/592 |
| 8,322,055 B1* | 12/2012 | Saint-Cyr | A61H 23/02 | 36/141 |
| 8,844,166 B2* | 9/2014 | Jazdanian | A43B 3/0005 | 36/43 |
| 9,030,335 B2* | 5/2015 | Ellis | A43B 1/0054 | 340/870.07 |
| 9,161,591 B2* | 10/2015 | Landau | A43B 7/1415 | |
| 9,955,749 B2* | 5/2018 | Van Atta | A43B 7/00 | |
| 9,993,388 B2* | 6/2018 | Park | A61H 39/04 | |
| 2003/0120190 A1 | 6/2003 | Miotto et al. | | |
| 2004/0177531 A1* | 9/2004 | DiBenedetto | A43B 1/0054 | 36/132 |
| 2004/0230146 A1* | 11/2004 | Chang | A43B 7/1465 | 601/134 |
| 2006/0036197 A1* | 2/2006 | Liu | A43B 3/0005 | 601/15 |
| 2006/0235465 A1* | 10/2006 | Koo | A43B 1/0054 | 606/204 |
| 2009/0107009 A1* | 4/2009 | Bishop | A43B 1/0027 | 36/114 |
| 2009/0149899 A1* | 6/2009 | Ahn | A43B 3/0005 | 607/3 |
| 2012/0130292 A1 | 5/2012 | Benjoar | | |
| 2012/0186101 A1* | 7/2012 | Sanchez | A43B 3/0005 | 36/44 |
| 2012/0260531 A1* | 10/2012 | Shi | A43B 3/0015 | 36/102 |
| 2013/0211290 A1* | 8/2013 | Lee | A43B 3/0005 | 600/592 |
| 2014/0298667 A1 | 10/2014 | Alkhalaf | | |
| 2016/0116327 A1* | 4/2016 | McCaskill | G01G 21/22 | 177/1 |

\* cited by examiner

200

FIG. 9
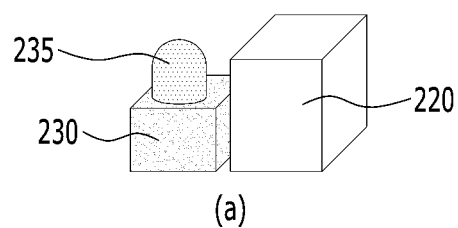
(a)
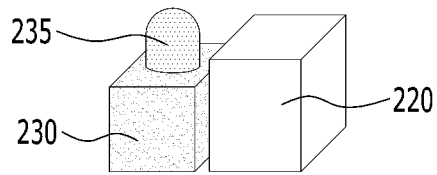
(b)
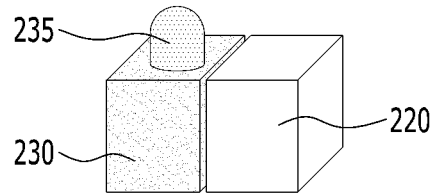
(c)

FIG. 13
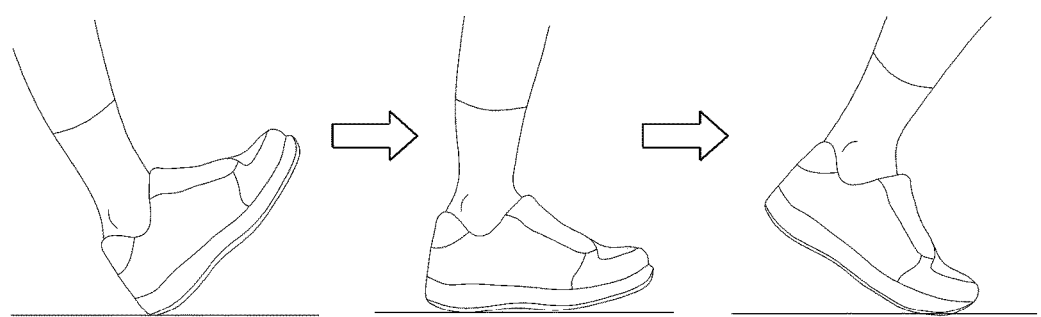
(a)
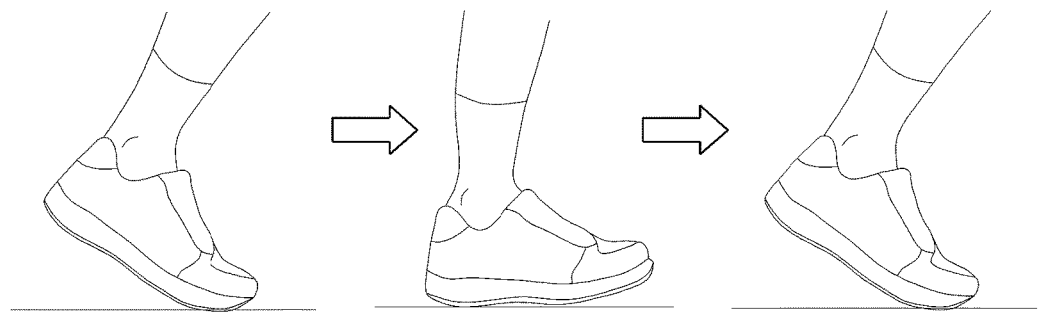
(b)

FIG. 21
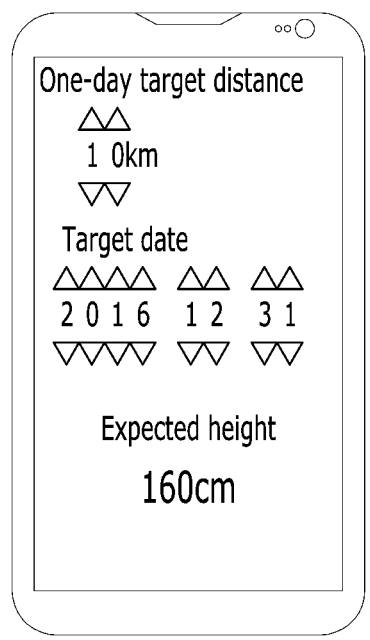
(a)
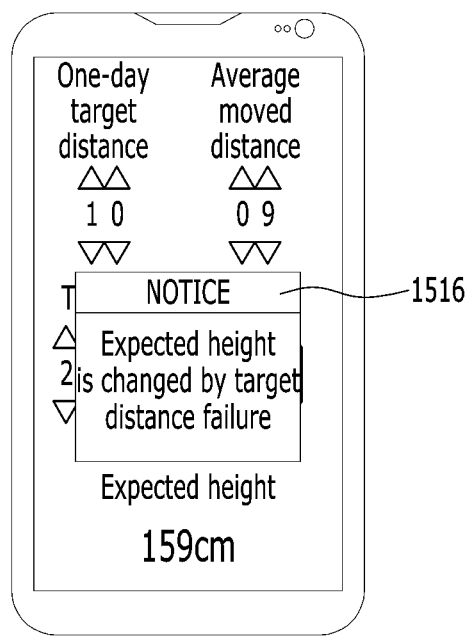
(b)

MOBILE TERMINAL, WIRELESS CHARGER AND WEARABLE DEVICE

CROSS-REFERENCE TO RELATED APPLICATIONS

This application claims priority to Korean Patent Application No. 10-2015-0027876 filed on Feb. 27, 2015 in Korea, the entire contents of which is hereby incorporated by reference in its entirety.

BACKGROUND OF THE DISCLOSURE

Field of the Disclosure

Embodiments of the present disclosure relate to a wearable device having an acupressure function, a wireless charger for charging the wearable device and a mobile terminal using the wearable device having the acupressure function.

Background of the Disclosure

Terminals may be generally classified as mobile/portable terminals or stationary terminals according to their mobility. Mobile terminals may also be classified as handheld terminals or vehicle mounted terminals according to whether or not a user can directly carry the terminal.

Mobile terminals have become increasingly more functional. Examples of such functions include data and voice communications, capturing images and video via a camera, recording audio, playing music files via a speaker system, and displaying images and video on a display. Some mobile terminals include additional functionality which supports game playing, while other terminals are configured as multimedia players. More recently, mobile terminals have been configured to receive broadcast and multicast signals which permit viewing of content such as videos and television programs.

As such functions become more diversified, the mobile terminal can support more complicated functions such as capturing images or video, reproducing music or video files, playing games, receiving broadcast signals, and the like. By comprehensively and collectively implementing such functions, the mobile terminal may be embodied in the form of a multimedia player or device.

Meanwhile, wearable mobile devices have been released which can be worn on users' body parts to acquire information on users' body parts or to affect the users' body parts. Even tests, treatment and cares performed only in a state where an examinee has to be standing or lying still may be facilitated, using such a wearable device usually wearable on a user's body part. Accordingly, types and functions of such wearable devices are diversified.

SUMMARY OF THE DISCLOSURE

An object of the present disclosure is to provide a wearable device having an acupressure function, a charger for charging the wearable device and a mobile terminal for controlling the wearable device having the acupressure function through synchronization with the wearable device.

Embodiments of the present disclosure may provide a wearable mobile terminal including a base provided in an insole of a shoe; a pressure sensing unit provided in the base to sense a pressure selectively applied when a user walks; an acupressure unit provided to apply an acupressure to the user's foot, when the pressure is applied to the pressure sensing unit; and a wireless communication unit synchronized with an external mobile terminal.

The pressure sensing unit may include a flexible cushion having a fluid injected therein and a fluid passage connected with an internal space of the cushion to the acupressure unit, and the acupressure unit is arranged in an inner portion of the shoe with respect to the user's ankle bone and the acupressure unit comprises an acupressure projection connected with the fluid passage to be projected when the fluid is flowing.

The acupressure projection may be arranged adjacent to a circumference of the ankle bone or under the ankle bone.

The wearable device may further include a curvature measurer provided in a lateral surface of the user's ankle; and a control unit provided to sense curvature variation measured by the curvature measurer and to control the acupressure projection to be positioned in a point having a large curvature.

The wearable device may further include a battery supplying an electric power; and a wireless charging coil provided in the base to flow electric current there through to be charged when placed in an external electromagnetic field.

The wearable device may further include a fixing unit coupled to an ankle portion of the shoe and coupled to the acupressure unit by a hinge; an acupressure projection projected from a first side of the acupressure toward the user's ankle; and a wire having one end coupled to the opposite side of the first side of the acupressure unit and the other one coupled to the pressure sensing unit, wherein the wire receives a tensile force when the user is walking and the acupressure unit is rotated on the hinge, and the acupressure projection is pressed toward the user's ankle.

The fixing unit may be coupled to a heel portion of the shoe, and a pair of acupressure units may be provided in both sides of the fixing unit, respectively, and the acupressure projection is provided between the user's ankle bone and Achilles tendon.

The wearable device may further include a plurality of pressure sensing units and a plurality of acupressure units; and a control unit control the plurality of the acupressure units to be projected selectively based on the pressure applied by the pressure sensing unit.

The wearable device may further include a control unit control one of the acupressure modules to be projected, when the order of the pressure variation sensed by the pressure sensing unit is different from a preset order of pressure variation, wherein an acupressure module comprises the pressure sensing unit and the acupressure unit and the plurality of the acupressure modules are arranged along a longitudinal direction of the base.

The wearable device may further include a battery supplying an electric power to the acupressure unit; and a control unit, wherein the acupressure unit is an electroactive polymer having a variable profile when a voltage is applied thereto, and the control unit applies a first-leveled voltage corresponding to a first height variation of the acupressure unit to the acupressure unit, and measures a second height variation of the acupressure unit based on the pressure variation sensed by the pressure sensing unit, and calculates a compensated voltage having a level corresponding to a difference between the first height variation and the second height variation, when the first height variation is different from the second height variation, and applies a pressure compensated as much as the compensated voltage to the acupressure unit.

Embodiments of the present disclosure may also provide a wireless charger including a wireless charger panel measuring the weight of the user standing on a top surface thereof, the wireless charger comprising a wireless electric power transmission coil; a height measuring sensor provided on a ceiling vertically over the wireless charging panel to measure the user's current height when the user is standing on the wireless charging panel; and a wireless communication unit transmitting data on the current height measured by the height measuring sensor and the weight measured by the wireless charging panel to an external mobile terminal.

The wireless charger may further include a height input unit receiving an input of the user's current height; a wireless communication unit synchronized with a wearable device having an acupressure function for practicing acupressure treatment to a walking user's foot; and a user input unit receiving input of a walking target distance.

Embodiments of the present disclosure may also provide a mobile terminal including a height input unit receiving a user's current height; a wireless communication unit synchronized with a wearable device having an acupressure function for practicing acupressure treatment to a walking user's foot; a user input unit receiving input of a target walking distance and a target walking time; and a control unit calculating an expected height based on the user's current height, the target walking distance and the target walking time.

The mobile terminal may further include a GPS receiving location information of the mobile terminal, wherein the control unit calculates the user's moved distance based on change of the location information received by the GPS, and when there is a difference between the user's moved distance and one-day target of the target walking distance, the control unit corrects an expected height.

The control unit may adjust the expected height, when the current height is renewed.

The wearable device may include an acupressure unit applying a pressure to a lateral surface of the user's ankle and a curvature measurer provided sensing curvature variation generated when the user is walking, and the control unit may calculate a precise position of the user's ankle bone based on the curvature variation measured by the curvature measurer and controls the wireless communication unit to transmit a command for controlling a position of the acupressure unit provided in the wearable device.

The user's step may be calculated based on the user's current height and the target distance is calculated as the step count, and the expected height may be calculated based on the step count.

The control unit may control an indicator to be output on a display unit to indicate a status of the wearable device, and the status of the wearable device may include one of walking, charging, low battery remains and synchronization checking.

The control unit may provide an alarm notifying the user of failure of one-day target distance, using an external mobile terminal, when one-day moved distance fails to reach one-day target distance of the target walking distance.

Embodiments of the present disclosure may also provide a mobile terminal including a wireless communication unit synchronized with a wearable device comprising a plurality of acupressure units pressing acupressure points of a sole of the user's foot; and a display unit providing a menu to set an acupressure point of the sole of the user's foot; and a control unit controlling the wireless communication unit to transmit an acupressure command for driving an acupressure unit corresponding to the set acupressure point. Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below and the accompanying drawings, which are given by illustration only, and thus are not limitative of the present invention, and wherein:

FIG. 9 is a diagram illustrating an acupressure module loaded in the wearable device in accordance with the present disclosure;

FIG. 13 is a diagram illustrating one example of normal and abnormal walks;

FIGS. 19 through 21 are diagrams illustrating setting of a height growth application, using the mobile terminal in accordance with the present disclosure;

DESCRIPTION OF SPECIFIC EMBODIMENTS

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, terms such as "module" and "unit" may be used to refer to elements or components. Use of such terms herein are merely intended to facilitate description of the specification, and the terms themselves are not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be directly connected with the other element or intervening elements may also be present. In contrast, when an element is referred to as being "directly connected with" another element, there are no intervening elements present.

A singular representation may include a plural representation unless it represents a definitely different meaning from the context. Terms such as "includes" or "has" are used herein and should be understood that they are capable of indicating an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

Figure 1:
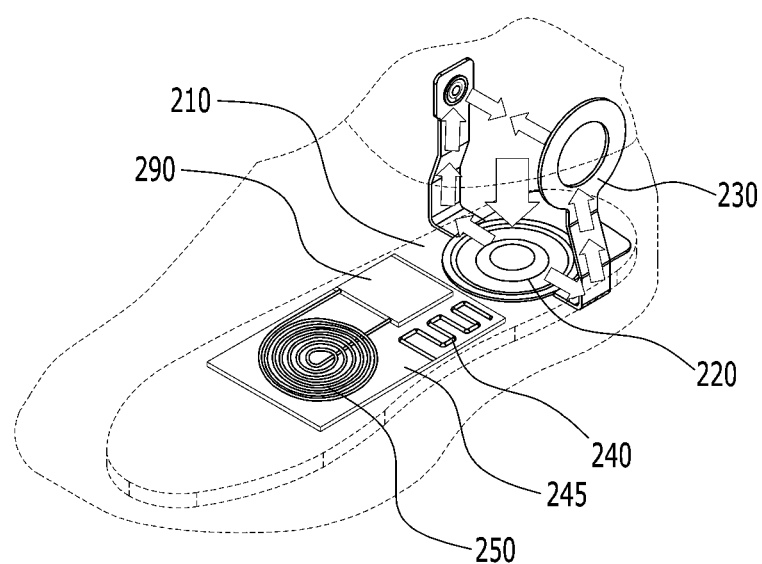
FIG. 1 is a diagram illustrating a wearable terminal in accordance with the present disclosure.
Figure 2:
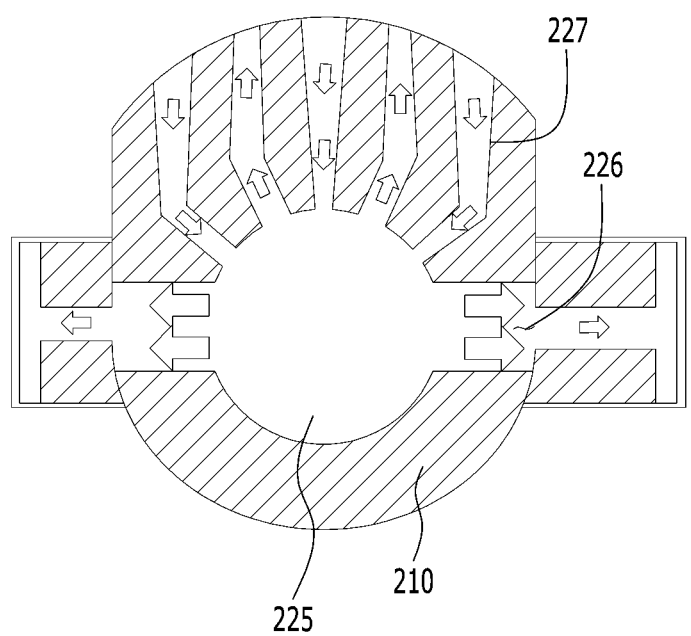
FIG. 2 is a sectional diagram illustrating a pressure sensor unit shown in FIG. 1.

FIG. 1 is a diagram illustrating a wearable device 200 in accordance with one embodiment of the present disclosure. A wearable device 200 in accordance with the present disclosure is worn on a user's foot. Examples of the wearable device 200 include a shoe and an insole for a shoe.

The wearable device 200 includes a base 210 disposed under a sole of the user's foot, a pressure sensing unit 220 provided in the base 210 to receive a pressure selectively applied when the user is walking, and an acupressure unit 230 applying a pressure to the user's foot when the pressure is applied to the pressure sensing unit 220.

The base 210 may be an insole disposed in a shoe and it may have a profile corresponding to an overall size of the sole of the user's foot or to some area of the sole.

When a person is walking or running, points at the sole which the user's weight is put on. Accordingly, the weight is uniformly put on the sole when the user is standing still and a strong pressure is applied to specific points of the sole when the user starts to walk or run.

The pressure sensing unit 220 may have a changeable profile or generate an electrical signal, according to change of a pressure applied to the foot when the user is walking. The pressure sensing unit 220 in accordance with this embodiment may be disposed in a portion of the insole, corresponding to the user's heel. The pressure sensing unit 220 may be disposed in a portion of the insole, corresponding to the user's a ball of the user's foot. For purposes of explanation, in this embodiment, the pressure sensing unit 220 is disposed on the portion corresponding to the heel of the user's foot. When the user initially sets the feet on the floor in walking, the strongest power is applied to the pressure sensing unit 220 provided in the portion of the sole corresponding to the user's heel.

The pressure sensing unit 220 in accordance with this embodiment may include a cushion formed of a flexible material, with a fluid injected therein. The cushion is formed of a flexible material having a predetermined elasticity such as silicon and rubber and a changeable profile of the cushion can be restituted to an original profile. The fluid injected in the cushion 225 may be gas such as air or a gel type liquid.

Fluid passages 226 are connected to right and left sides of the cushion, respectively. When the user puts the foot on the ground, the force is applied to the pressure sensing unit 220 and the fluid inside the cushion 225 is pushed and moved to the fluid passages 226. When the fluid is gas, another fluid passage 227 connected to the outside may be further provided and the fluid passage 227 in communication with the outside may prevent rupture of the cushion. The fluid passage 226 is extended along the acupressure unit 230 extended to the user's ankle.

An acupressure projection 235 is provided in an end of the acupressure unit 230 and the acupressure projection 235 is formed of the same flexible material equal for the cushion. The fluid of the cushion inside 225 moves along the fluid passage 226 and reaches the acupressure projection 235. In this instance, the acupressure projection 235 is expanded to perform an acupressure treatment for the user's foot.

The acupressure unit 230 of the present disclosure applies acupressure treatment near the user's ankle, more specifically, near the ankle bone. A growing point is arranged near the ankle bone and growth may be promoted, when applying the acupressure treatment to the ankle bone.

Figure 3:
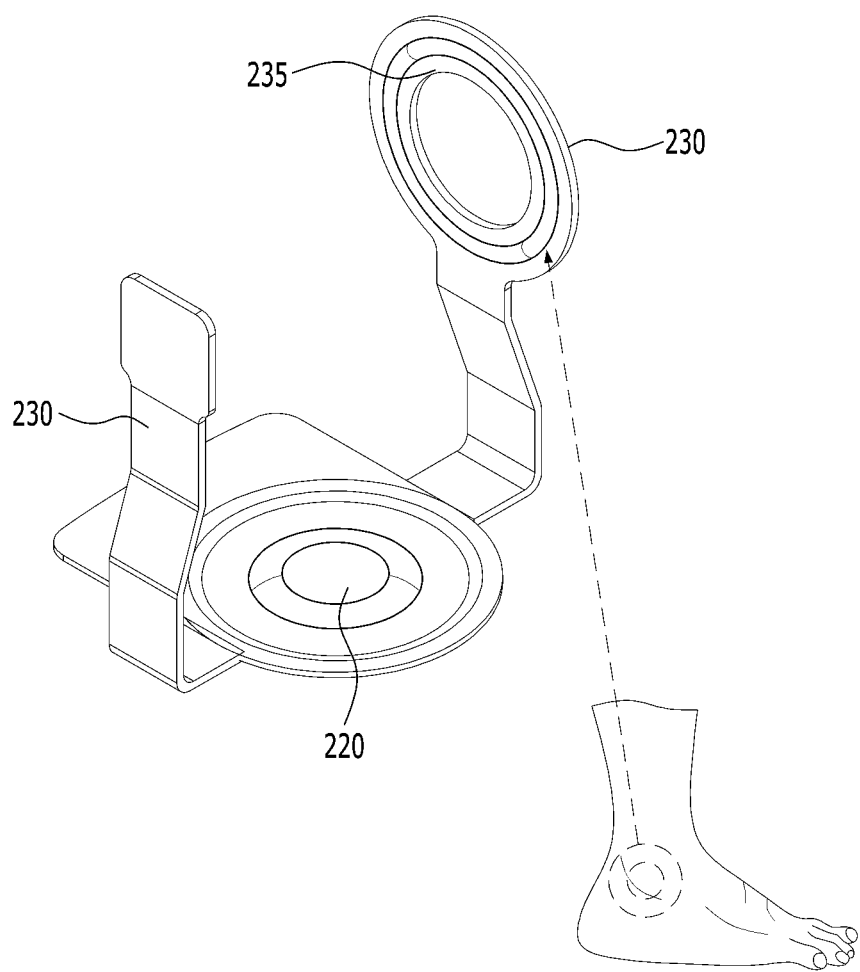
FIGS. 3 and 4 are diagrams illustrating an acupressure unit shown in FIG. 1.
Figure 4:
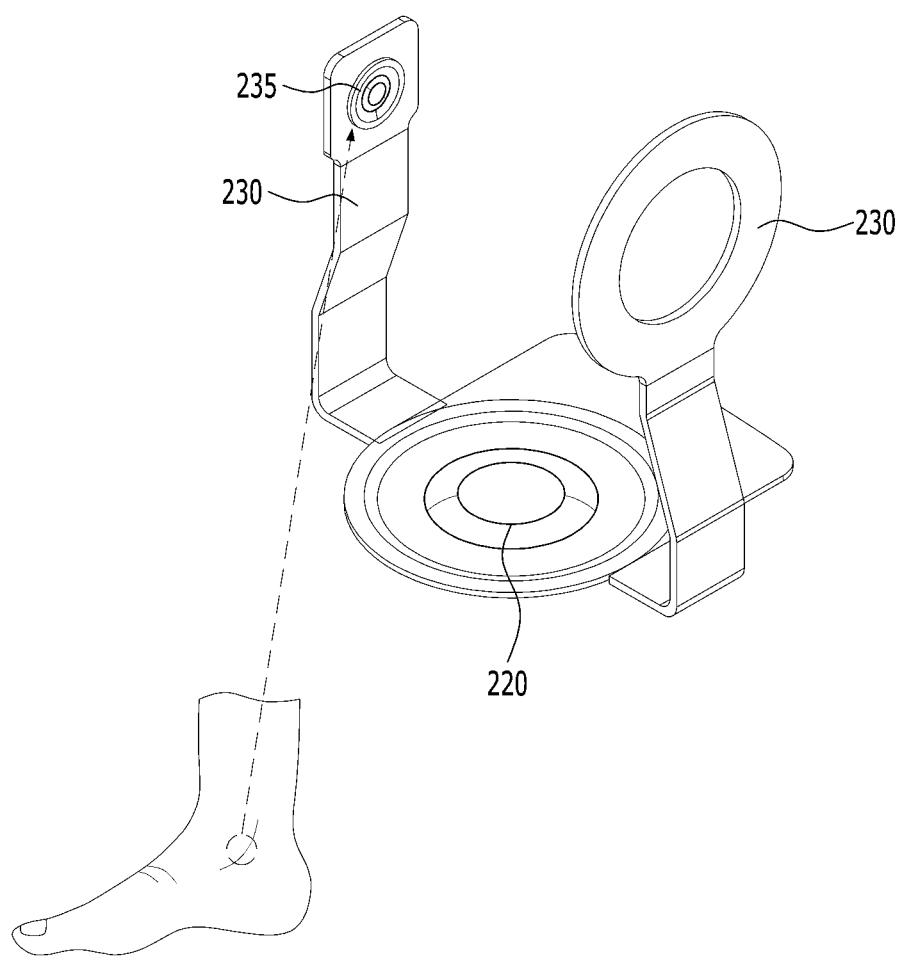
Figure 5:
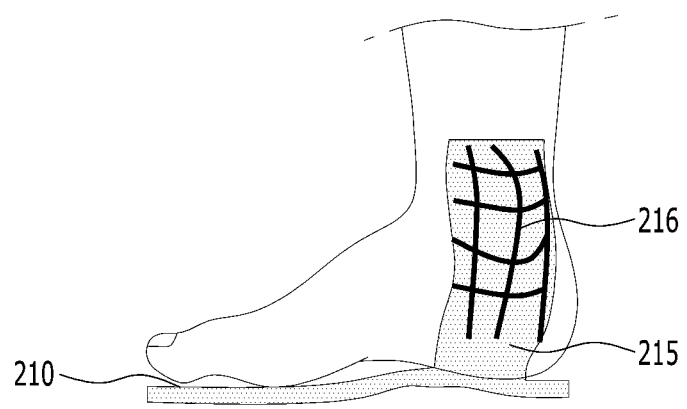
FIG. 5 is a diagram illustrating a curvature measurer provided in the wearable device in accordance with one embodiment of the present disclosure.

FIGS. 3 and 4 are diagrams illustrating the acupressure unit 230 shown in FIG. 1. FIG. 5 is a diagram illustrating a curvature measurer provided in the wearable device 200 in accordance with one embodiment of the present disclosure.

The acupressure projection 235 shown in FIG. 3 may have a ring shape for pressing an area near the ankle or a shape arranged under the ankle bone. The acupressure projection 235 in accordance with the embodiment is provided in each of inner and outer portions with respect to the ankle bone. A pair of acupressure projections 235 may be formed in the same shape shown in the drawing or a different shape.

The position of the ankle bone may be different for each person and a curvature measurer mechanism 216 is provided around a lateral surface of the user's ankle, in other words, around the ankle as shown in FIG. 5, to measure the location of the ankle. The position where the ankle bone is located is projected and a curvature is increased, so that the position having the increased curvature is determined as the position where the ankle bone is located and the position of the acupressure projection 235 can be changed.

The acupressure unit 230 and the acupressure projection 235 may be provided a portion corresponding to between toes, to the sole or a top side of the foot, not necessarily near the ankle bone. Whenever the user is walking, acupressure treatment is naturally practiced so that the user's growth is promoted or the user's stress is relieved effectively.

In addition, the wearable device 200 in accordance with the present disclosure may include a wireless communication unit and the wireless communication unit is connected with an external mobile terminal to check a current status. The number of the acupressure treatments may be transmitted. In case acupressure treatment is controlled according to control of the external mobile terminal, except the mechanical structured acupressure treatment in accordance with this embodiment, the wearable device 200 may include a wireless communication unit 240 for transmission and reception of a signal to and from the external mobile terminal.

The wireless communication unit 240 may facilitate transmission of even information on a battery status or a charging status of the wearable device 200 to the external device, only to check a status of the wearable device 200. In the drawings, the wireless communication unit 240 is formed in the base 210 or it may be formed in the acupressure unit 230.

In case it includes components requiring electricity such as the wireless communication unit, the wearable device 200 should include a battery 290 for supplying electricity and an interface unit for connecting a charging cable thereto so as to charge the battery 290. However, the wearable device 200 wearable on the foot is easily exposed to contaminants so that it is difficult to expose the interface for connection with the charging cable outside. In case the interface is embedded, the connection is difficult and the wearable device can be charged via a wireless charging method.

A wireless charging coil 250 for wireless charging is formed in the base 210. When the user approaches a charger 400 including a wireless power transmission coil 420, electric currents are flowing according to variation of the electromagnetic field formed by the wireless power transmission coil 420 and the wearable device is charged. The wireless charging coil 250 is arranged, not overlapped with an antenna 240 for wireless communication as possible, so that the performance of the antenna 240 and the performance of the wireless charging coil 250 cannot be deteriorated.

Figure 6:
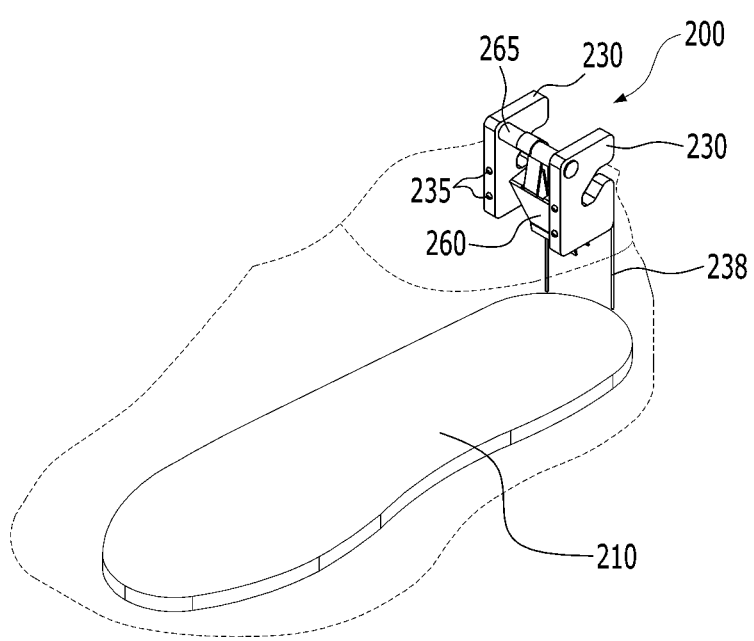
FIG. 6 is a diagram illustrating a wearable device in accordance with another embodiment of the present disclosure.
Figure 7:
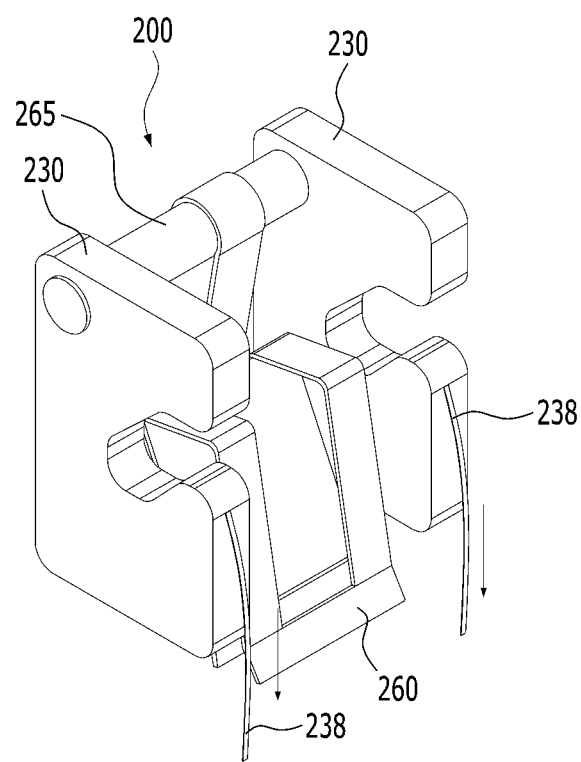
FIG. 7 is a diagram illustrating the wearable device shown in FIG. 6, in a different view.

FIG. 6 is a diagram illustrating a wearable device 200 in accordance with another embodiment of the present disclosure. FIG. 7 is a diagram illustrating the wearable device 200 shown in FIG. 6, in a different view. Referring to FIG. 6, the wearable device 200 according to this embodiment may include a fixing unit 260 fixed to a heel portion of a shoe to be coupled to the acupressure unit 230 by a hinge. When the fixing unit 260 is decoupled from the heel portion of the shoe, the insole-shaped wearable device 200 may be realized as a separable type separated from the shoe.

The acupressure unit 230 rotatably coupled to right and left sides of the fixing unit 260 by a hinge shaft 265. In the drawing, a pair of acupressure units are shown but one acupressure unit 230 may be provided in one of the sides or more acupressure units 230 are coupled to the fixing unit 260 by a hinge. The fixing unit 260 is fixed to the shoe and the acupressure unit 230 is rotated on the hinge shaft 265 and the acupressure projection 235 projected from a front surface of the acupressure unit 230 (a direction in which the user's foot is located) practices the user's foot.

Acupressure treatment practicing for a recessed area (a growing point) between Achilles tendon and the anklebone above the heel may help growth. The acupressure unit 230 in accordance with this embodiment practices acupressure treatment on the growing point, while rotated on the hinge. The acupressure treatment point may be differentiated by the length of the acupressure unit 230 so that growing points at other points can be pressed.

To apply the force to rotate the acupressure unit 230, the acupressure unit 230 is connected with the heel portion of the insole 210 of the shoe via a wire 238. The heel portion of the insole of the shoe is the pressure sensing unit 220. When contacting with the insole, the user's heel presses the pressure sensing unit 220.

When the user's heel contacts with the ground, Achilles tendon is increased. When the heel is separated from the ground and the toes support the weight, Achilles tendon is decreased. In other words, while walking, a distance between the heel of the shoe and the user's heel is changed repeatedly, so that a distance between the insole (i.e., the base) 210 and the acupressure unit 230 may be changed.

Using the characteristic, one end of the wire 238 may be connected to the acupressure unit 230 and the other end of the wire 238 may be connected to the heel-corresponding portion of the base 210 of the shoe. When the heel contacts with the ground, the wire 238 applies a tension to the acupressure unit 230. When the heel is separated from the ground and the toe-corresponding portion supports the ground, the tension of the wire 238 is removed and the acupressure unit 230 is restituted to the original position.

When the tension is applied, the wire 238 may be connected to the acupressure unit 230 in the reverse direction of the direction in which the acupressure projection 235 is formed, for the acupressure projection 235 of the acupressure unit 230 to be projected toward the user's ankle.

Figure 8:
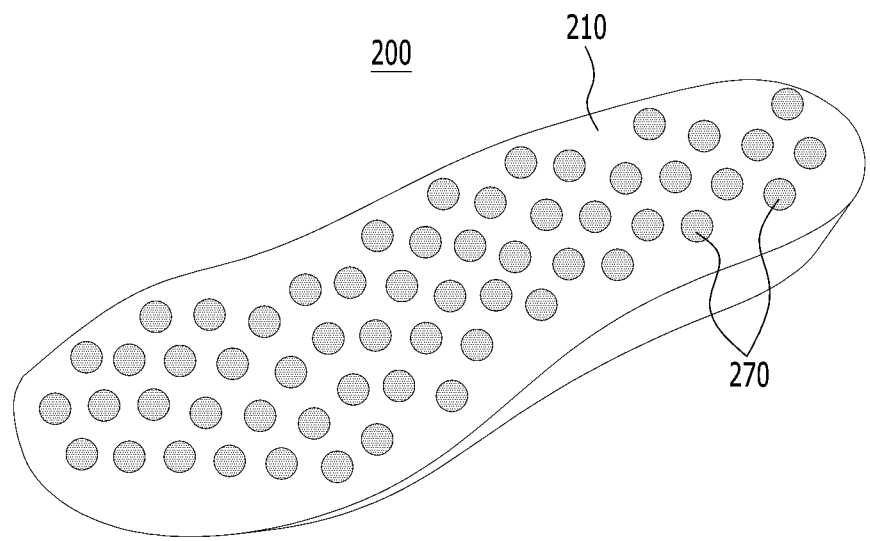
FIG. 8 is a diagram illustrating a wearable device in accordance with a further embodiment of the present disclosure.

FIG. 8 is a diagram illustrating a wearable device 200 in accordance with a further embodiment of the present disclosure. In this embodiment, an acupressure module 270 may be arranged in the base 210 provided in an inner bottom of the shoe. The acupressure module 270 may include a pressure sensing unit 220 and an acupressure unit 230. When the pressure sensing unit 220 senses variation of the pressure, the variation of the pressure is transmitted to a control unit and the acupressure unit 230 projected according to control of the control unit 245 applies an acupressure to the user's sole.

A force sensing resistor may be used as the pressure sensing unit. When the pressure is applied, resistance changes and pressure variation is converted into a signal. An electroactive polymer may be used as the acupressure unit 230. When a voltage is applied to the electroactive polymer, a profile of the electroactive polymer is changed according to the size of the voltage.

The number and position of the acupressure modules 270 may be variable based on objects and areas of acupressure which will be practiced. For example, when the acupressure is practiced to promote growth, the acupressure is practiced between toes. To solve problems of shoulder discomfort and hand numbness, acupressure treatment is practiced in root areas from the second toe to the fifth toe.

FIG. 9 is a diagram illustrating an acupressure module 270 loaded in the wearable device 200 in accordance with the present disclosure. As shown in FIG. 9 (a), the acupressure module 270 is more projected than the acupressure unit 230. The acupressure unit 230 includes the acupressure projection 235 and only the acupressure projection may be projected. Alternatively, the length of the acupressure unit 230 is changed to be more projected toward the user's foot.

A predetermined portion of the acupressure unit 230 which requires acupressure treatment may be selectively projected. A portion of the acupressure unit 230 may be less projected as shown in (b) or more projected as shown in (c). The projection degree may be determined by the user or controlled to be differentiated according to the strength of the pressure applied to the pressure sensing unit 220.

For example, even though the acupressure unit 230 is not projected a lot, the strong pressure is applied to the portion of the pressure sensing unit 220 already receiving the pressure. Only the acupressure unit 230 provided in the portion receiving the less pressure may be more projected.

Figure 10:
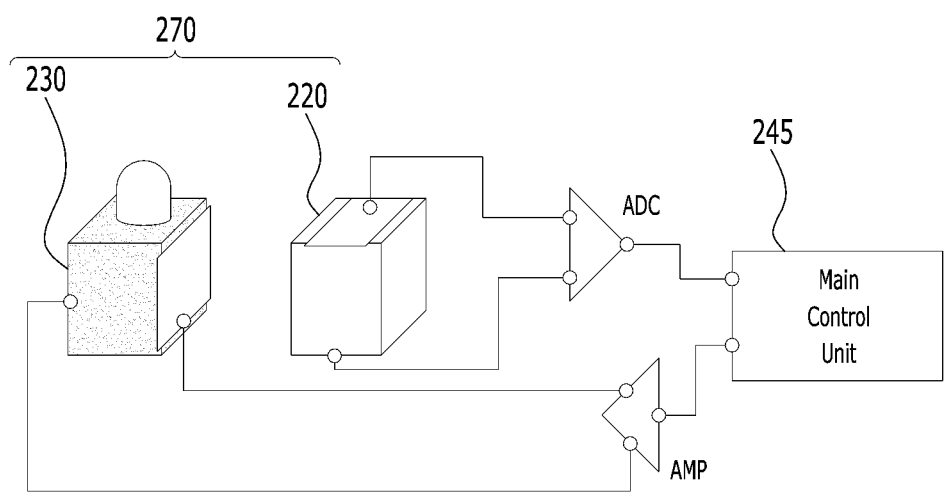
FIG. 10 is a diagram illustrating one embodiment of a circuit system of the acupressure module loaded in the wearable device in accordance with one embodiment of the present disclosure.

FIG. 10 is a diagram illustrating one embodiment of a circuit system of the acupressure module 270 loaded in the wearable device in accordance with one embodiment of the present disclosure. ADC (Analog Digital Converter) of the pressure sensing unit 220 senses a resistance changing when a pressure is applied and the resistance variation is transmitted to the control unit. The control unit applies a boosted voltage to the acupressure unit 230 through AMP (Amplifier).

The pressure sensed by the pressure sensing unit 220 is variable according to variation of the profile of the acupressure unit 230. Data for profile variation of the acupressure unit 230 may be collected based on the pressure variation. As the profile of the acupressure unit 230 is repeatedly varied, the acupressure unit 230 is deteriorated. Accordingly, there could be a difference among profile variation values, even when the equal voltage is applied.

The battery for supplying the electric power applied to the acupressure unit 230 may be connected to an external charger via a wire or wirelessly, to be charged. Alternatively, the battery may include a piezoelectric element to supply the electric power. When an external pressure is applied thereto, the piezoelectric power generates electric charge in proportion to the external pressure and it stores the generated electric charge therein. The walking user applies a pressure or force to a bottom or an insole of the shoe or a varied curvature of the bottom of the shoe is varied. The energy generated at this time may be used later as the electric power for changing the profile of the acupressure unit 230.

Figure 11:
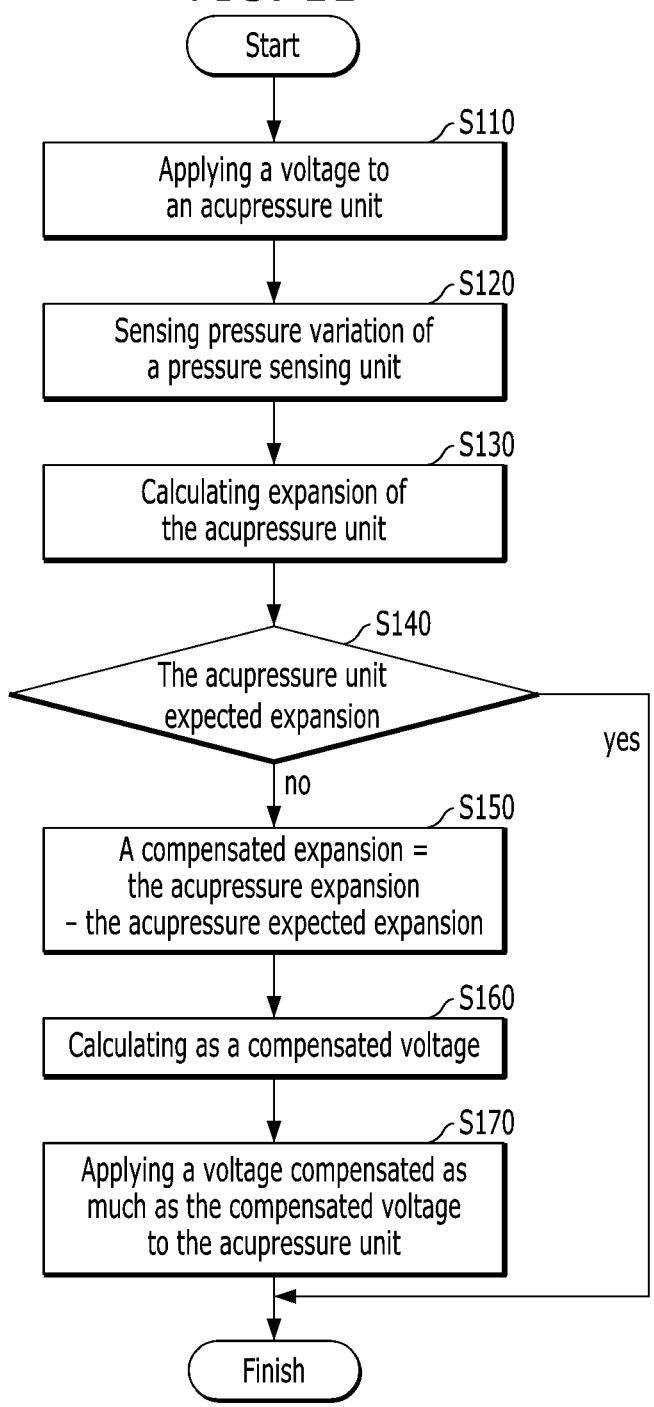
FIG. 11 is a diagram illustrating a control method of the acupressure module loaded in the wearable device in accordance with one embodiment of the present disclosure.

FIG. 11 is a diagram illustrating a control method of the acupressure module loaded in the wearable device in accordance with one embodiment of the present disclosure. The pressure sensing unit 220 may compensate and correct errors caused by the deterioration of the acupressure unit 220.

As shown in FIG. 11, a predetermined leveled voltage is applied to the acupressure unit (S110). The predetermined level of the voltage is corresponding to a level high enough to change the profile of the acupressure unit 230 corresponding to the projected height of the acupressure projection calculated by the control unit 245. The pressure sensing unit 220 senses variation of the pressure according to variation of the profile of the acupressure unit 230. The strength of the pressure sensed by the pressure sensing unit 220 is decreased according to the projected height of the acupressure unit 230. The control unit may calculate the expanded degree of the acupressure unit based on the varied pressure sensed by the pressure sensing unit (S130). When the calculated expansion degree of the acupressure unit (the calculated expansion value) is not equal to the expansion degree achieved by the predetermined-leveled voltage (the predetermined expansion value) (S140), it is determined that the acupressure unit is deteriorated and a compensated expansion value (S150) which is a difference between the values is calculated. A voltage of a corresponding level to the compensated expansion value (the compensated voltage) is calculated (S160). The level of the former voltage applied to the acupressure is compensated as much as the compensated voltage and the compensated voltage is applied to the acupressure unit (S170). In this instance, even the deteriorated acupressure unit 230 may be used continuously and the usage life of the wearable device may be increased.

Figure 12:
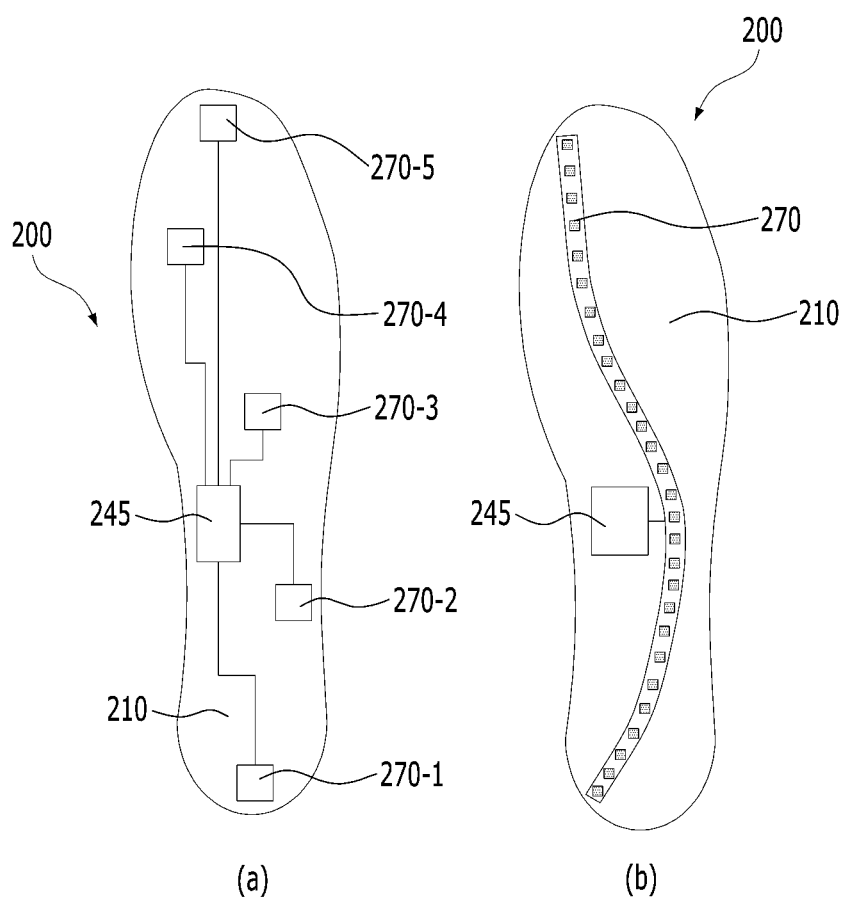
FIG. 12 is a diagram illustrating a wearable device in accordance with a further embodiment of the present disclosure.

FIG. 12 is a diagram illustrating a wearable device 200 in accordance with a further embodiment of the present disclosure. The wearable device 200 includes the acupressure module 270 having the pressure sensing unit 220 and the acupressure unit 230 and the control unit 245 receiving the pressure sensed by the acupressure module 270 and controlling the acupressure unit 230 (S230).

FIG. 13 is a diagram illustrating one example of normal and abnormal walks. As shown in (a), it is the right walking that a person is walking, having from the heels to the toes touching the ground in order. A central inner portion of a human insole is spaced apart a distance from the ground so that a stronger pressure is normally applied to an outer portion of the foot even when a person is walking.

A person having a wrong way of walking is walking, with the toes firstly touching the ground or with applying a strong force to the outer portion of the foot as shown in (b). However, as shown in FIG. 12, acupressure modules 270 are arranged along the right points the force has to be applied in order when the user is walking and the acupressure modules sense that the force is applied to appropriate points in a preset order. When sensing a weaker force than the predetermined pressure, the control unit 245 determines that the user is walking in a wrong way. When the user is walking in the wrong way, the control unit 245 controls the acupressure unit 230 to be projected and applies the force to the user's foot so as to warn the wrong way of walking. When the force is applied to the user's foot, the user recognizes the wrong way of walking and corrects the wrong way.

Figure 14:
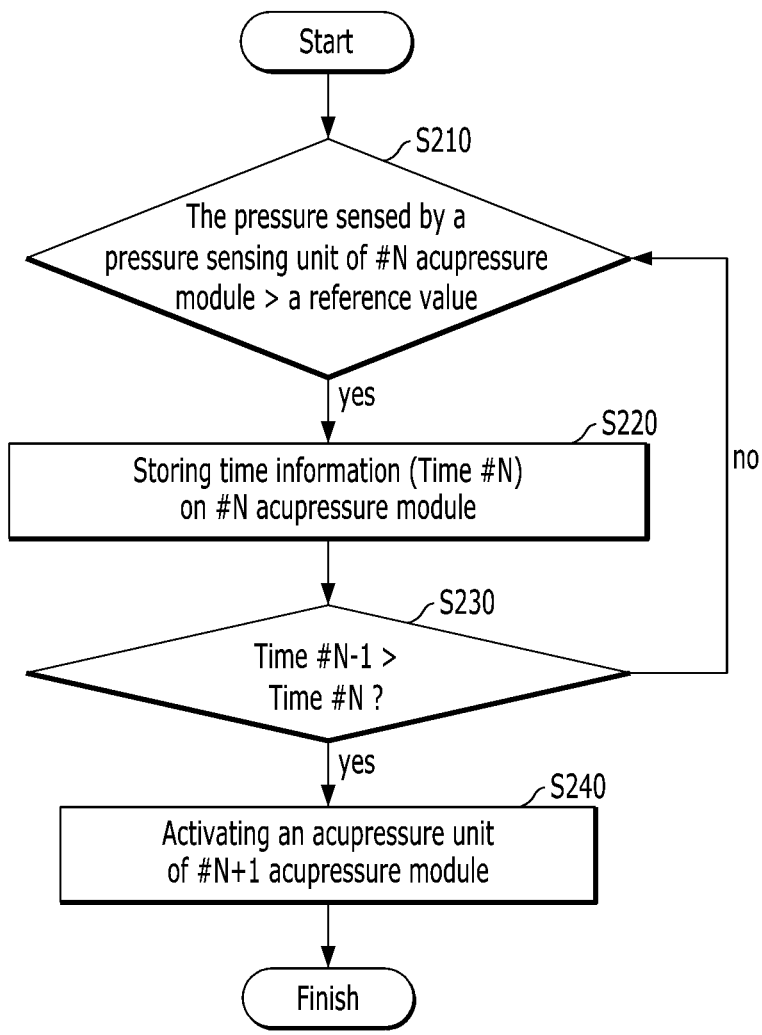
FIG. 14 is a flow chart illustrating a method for correcting a walk, using the wearable device in accordance with the present disclosure.

As shown in FIG. 14 which is a flow chart illustrating a method for correcting a walk, using the wearable device in accordance with the present disclosure, it is determined that the user steps on foot, when the pressure sensed by the pressure sensing unit of the $n^{th}$ acupressure module is stronger than a reference value (S210), and information on the time when the pressure is sensed (Time #N) is stored (S220). The order of the acupressure modules is shown in FIG. 12 and they are numbered from the heel in order as shown in FIG. 12.

In other words, the pressure is sensed in the order of increasing N, in case of normal walling (see FIG. 13 (a)). The pressure is sensed in a different order from the order of increasing N, in case of abnormal walking (see FIG. 13 (b)).

When time information (Time #N−1) of one acupressure module arranged behind the heel is larger than time information (Time #N) of another acupressure module arranged near the toes, the pressure is applied to the (N−1)$^{th}$ acupressure module later than to the N$^{th}$ acupressure module and it may be determined that the user's walking is the abnormal walking (S230). To warn the user that the user's walking is the abnormal walking, an acupressure unit of one acupressure module as the next one the pressure has to be applied to (the (N+1)$^{th}$ acupressure module is activated to correct the wrong way of walking into the right way (S240).

The acupressure modules 270-1 to 270-5 may be spaced apart a preset distance from each other along the points as shown in FIG. 12 (a). The acupressure modules 270 may be arranged continuously as shown in FIG. 12 (b).

Using the wireless communication unit 240, the wearable device 200 may communicate with an external mobile terminal. When the wireless communication unit 240 is provided, the control unit 245 may not be provided in the wearable device 200 necessarily and a control unit of the external mobile terminal may control the acupressure modules 270.

The wearable device 200 may simply transmit the pressure value sensed by the pressure sensing unit 220 to the external mobile terminal and the external mobile terminal may control the projection of the acupressure units 230.

Figure 15:
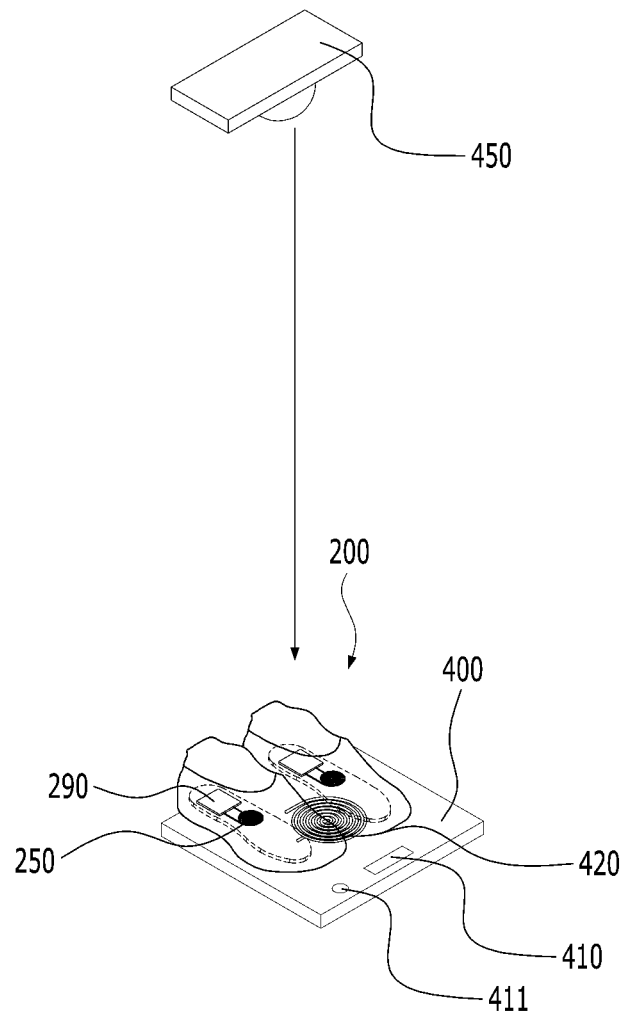
FIG. 15 is a diagram illustrating a wireless charger and the wearable device in accordance with the present disclosure.

FIG. 15 is a diagram illustrating a wireless charger 400 and the wearable device in accordance with the present disclosure. The wireless charger 400 includes a wireless electric power transmission coil 420. When electricity is applied to the wireless electric power transmission coil 420, electric currents flow along the wireless electric power transmission coil 420 to convert a nearby electromagnetic field. When a wireless charging coil 250 is disposed in the electromagnetic field, an electron of the wireless charging coil 250 is moved by the electromagnetic field and an electric power is generated.

When the wearable device 200 mentioned above is located in the wireless charger 400, electric currents flow to the wireless charging coil 250 arranged in the base 210 of the wearable device 200 and the battery of the wearable device 200 is charged.

The wearable device 200 in accordance with the present disclosure is worn on the user's foot. Accordingly, once the user steps on the wireless charger 400, having the wearable device 200 worn on the foot, the wireless charger 400 may measure the user's weight. At this time, in case data about the weight of the wearable device 200 is provided, the corresponding weight of the wearable device is subtracted from the overall weight.

Alternatively, using an infrared sensor 450 arranged vertically over the wireless charger 400, the height of the user standing on the wireless charger 400 may be measured. The infrared sensor 450 may be installed on the ceiling.

The infrared sensor 450 installed on the ceiling records a distance to the wireless charger 400 in an initial setting process. When the user steps on the wireless charger 400, the infrared ray sensor 450 may calculate the reduced distance as the user's height.

The infrared sensor 450 may transmit and receive a signal to and from the wireless charger 400. When the weight sensed by the wireless charger 400 is changed or the electromagnetic field is changed, it is determined that the user is standing on the wireless charger 400 and the infrared sensor 450 is operated.

The operating infrared sensor 450 emits infrared light on the head of the user standing on the wireless charger 400 and receives the reflected infrared light, to measure the user's height. Meanwhile, in case only the wearable device 200 is put on the wireless charger 200, the infrared sensor 450 may measure only the height of the shoe and not the user's height. When the measured height is smaller than a reference height, it is determined that no person is standing on the wireless charger and the value sensed by the infrared sensor may be ignored.

When a value for the height of the wearable device 200 is provided in case the user is wearing the wearable device 200 on the foot, the height of the wearable device 200 is subtracted from the overall height and the calculated value is the user's height. In case the user is wearing the wearable device 200, the electromagnetic field formed by the wireless electric power transmission coil 420 of the wireless charger is changed. Accordingly, when change of the electromagnetic field is sensed, the height of the wearable device 200 is subtracted from the value measured by the infrared sensor 450 and the calculated value is the user's height.

While measuring the user's weight and height, a voice guidance saying that you should not move and stand still while measuring the weight and height may be output. After the measuring is ended, an alarm sound notifying that the measurement is ended may be output through a lamp 411 or a display 410. In case the wireless charger 400 is in communication with an external mobile terminal, the measured user's height and weight may be transmitted to the external mobile terminal.

Figure 16A:
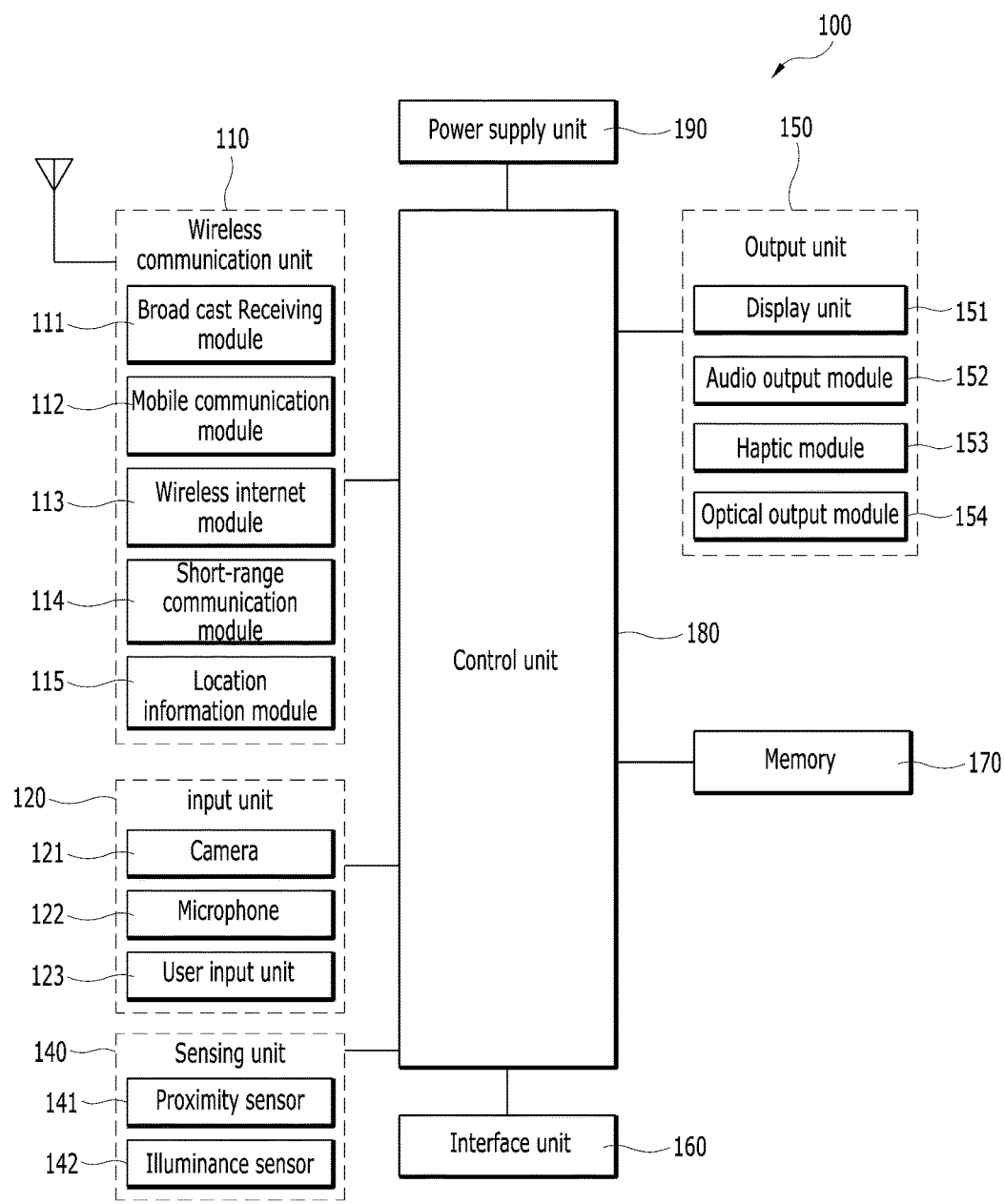
FIG. 16A is a block diagram of a mobile terminal in accordance with the present disclosure.
Figure 16B:
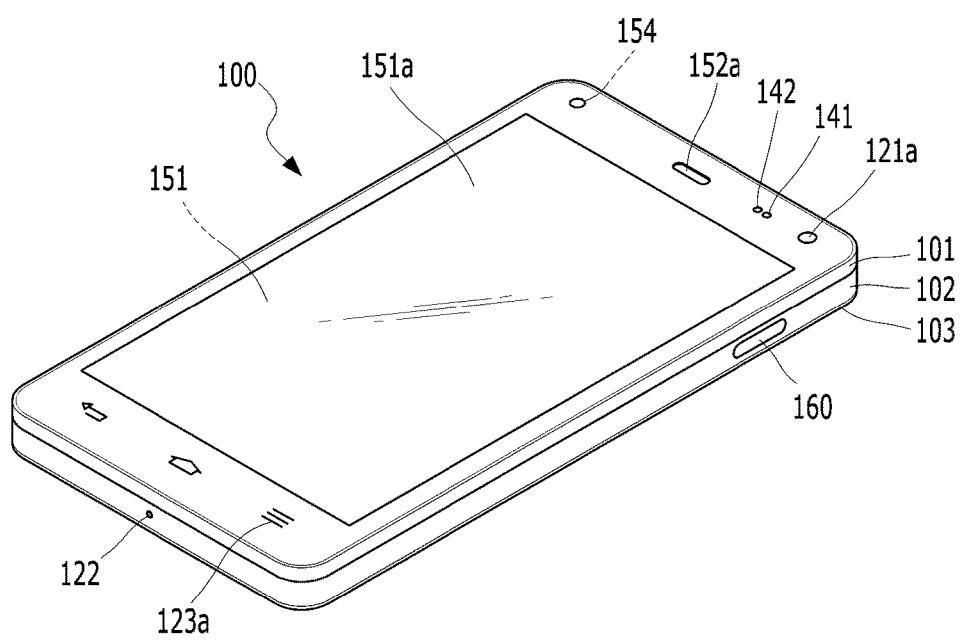
FIGS. 16B and 16C are conceptual views of one example of the mobile terminal, viewed from different directions.
Figure 16C:
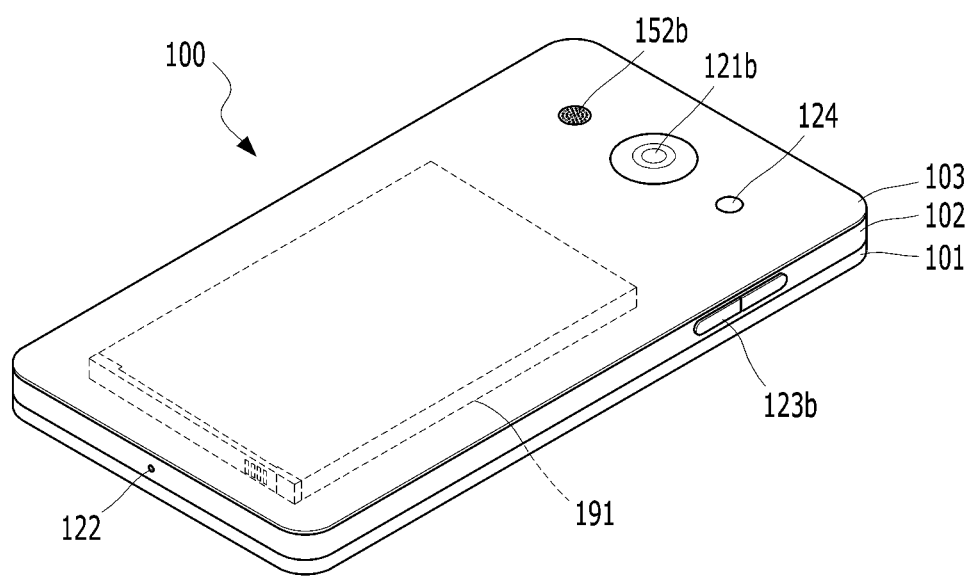

Reference is now made to FIGS. 16A-16C, where FIG. 16A is a block diagram of a mobile terminal in accordance with the present disclosure, and FIGS. 16B and 16C are conceptual views of one example of the mobile terminal, viewed from different directions.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

Referring now to FIG. 16A, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks.

To facilitate such communications, the wireless communication unit 110 includes one or more of a broadcast receiving module 111, a mobile communication module 112, a wireless Internet module 113, a short-range communication module 114, and a location information module 115.

The short-range communication module 114 may sense (or recognize) the wearable device 200 which can communicate with the mobile terminal in a short range near the mobile terminal 100. In case the sensed wearable device 200 is a device certified to communicate with the mobile terminal in accordance with the present disclosure, the control unit 180 may transmit at least predetermined amount of the data processed in the mobile terminal 100 to the wearable device 200 through the short-range communication module 114.

The user may use the data processed in the mobile terminal 100, using the wearable device 200. For example, the pressure sensing unit 220 of the wearable device 200, shown in FIG. 1, transmits the number of times the user pressing the pressure sensing unit 220 of the wearable device 200 with the foot to the mobile terminal 100, to count the number of time being pressed. Or, the strength of the pressure sensed by the pressure sensing unit 220 of the wearable device 200, shown in FIG. 8, is transmitted to the mobile terminal 100 and the mobile terminal 100 may figure out the way of the user's walking. A control command for driving the acupressure unit 230 configured to correct the user's posture and to practice an acupressure treatment for a specific area may be transmitted from the mobile terminal 100 to the wearable device 200, using the short-range communication module 114.

The short-range communication module 114 is configured for short range communication and may support short range communication, using one or more of Bluetooth™, RFID (Radio Frequency Identification), IrDA (Infrared Data Association), UWB (Ultra Wideband), ZigBee, NFC(Near Field Communication), Wi-Fi (Wireless-Fidelity), Wi-Fi Direct and Wireless USB (Wireless Universal Serial Bus). Such the short-range communication module 114 may support wireless communication between the mobile terminal 100 and a wireless communication system, between the mobile terminal 100 and another mobile terminal 100 or between the mobile terminal 100 and a network in which another mobile terminal 100 (or an external server) is located. The short range wireless communication network may wireless personal area network.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 16A, the sensing unit 140 is shown having a proximity sensor 141 and an illuminance sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154. The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs.

The controller 180 may provide or process information or functions appropriate for a user by processing signals, data, information and the like, which are input or output by the various components depicted in FIG. 16A, or activating application programs stored in the memory 170. As one example, the controller 180 controls some or all of the components illustrated in FIGS. 16A-16C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Referring still to FIG. 16A, various components depicted in this figure will now be described in more detail.

Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like).

Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illuminance sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a fluid passage to allow power from the cradle to be supplied to the mobile terminal 100 or may serve as a fluid passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Figure 17:
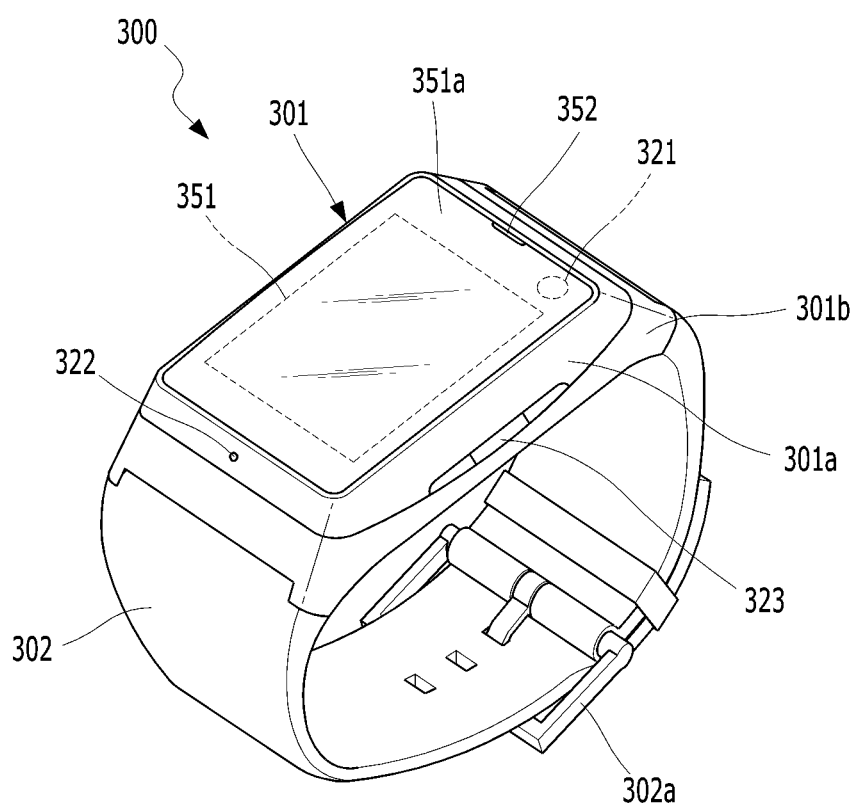
FIG. 17 is a conceptual diagram illustrating a mobile terminal in accordance with another embodiment of the present disclosure.
Figure 18:
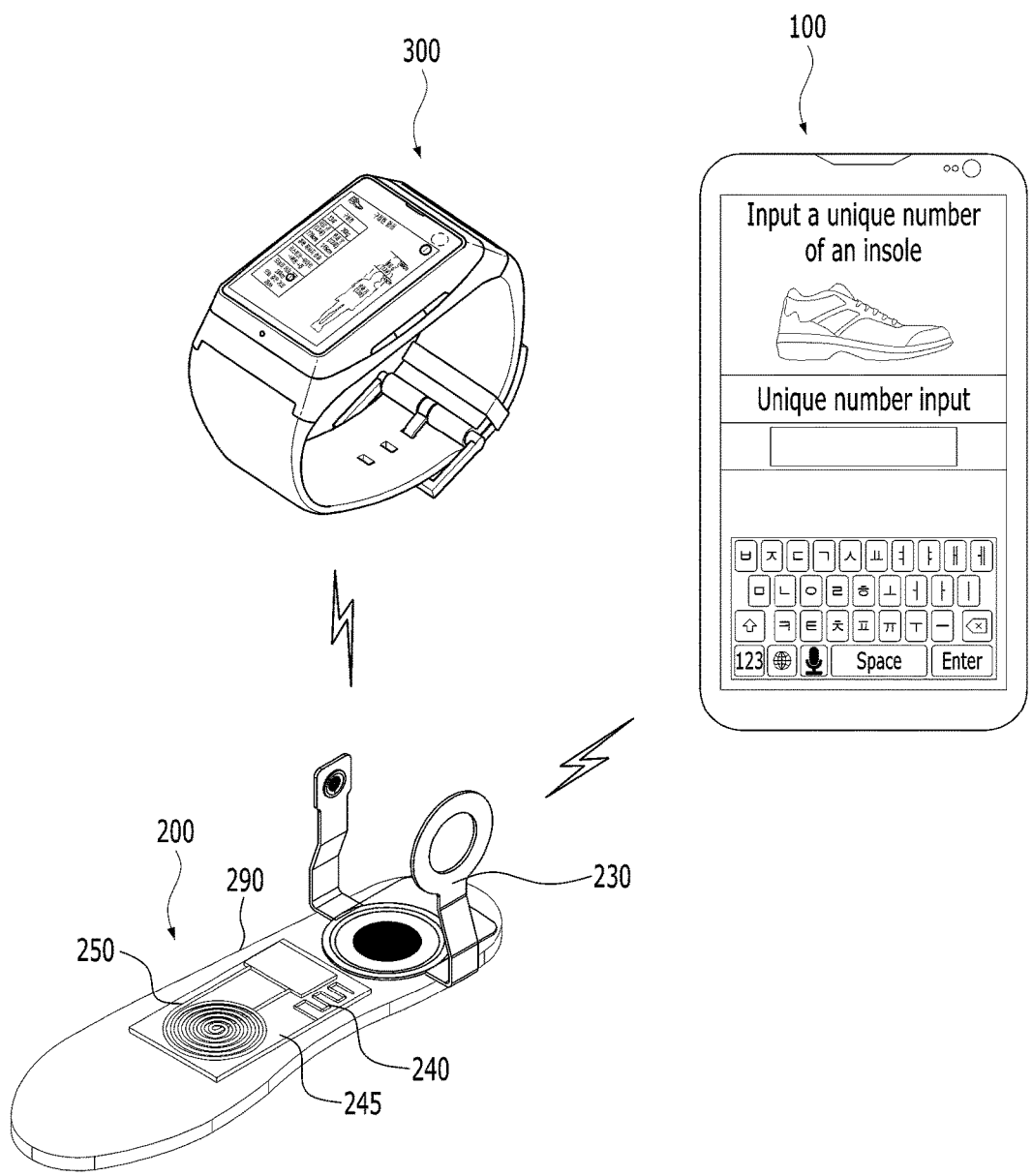
FIG. 18 is a diagram illustrating synchronization between the mobile terminal and the wearable device in accordance with the present disclosure.

FIG. 17 is a conceptual diagram illustrating a mobile terminal in accordance with another embodiment of the present disclosure. The mobile terminal in accordance with this embodiment may be a watch type mobile terminal 300 which can be worn on the user's wrist as a portable device. As shown in FIG. 18, the watch type mobile terminal 300 may exchange data with the mobile terminal 100 or the wearable device 200 and control a connected device, when synchronized with the mobile terminal 100 or the wearable device 200.

Referring to FIG. 17, the watch type mobile terminal 300 includes a main body 301 having a display unit 351 and a band 302 connected to the main body 301 to make the main body 301 worn on the wrist easily. Typically, the mobile terminal 300 may include the characteristics of the mobile terminal 100 shown in FIGS. 16A-16C or similar characteristics.

The main body 301 includes a case which defines a profile thereof. As shown in the drawing, the case may include a first case 301a and a second case 301b which define an internal space where diverse electronic components are provided. However, the main body 301 in accordance with the present disclosure is not limited thereto. One case may be provided to define the internal space and a mobile terminal 300 having the uni-body may be realized.

The watch type mobile terminal 300 may facilitate wireless communication and an antenna may be installed in the main body 301 for the wireless communication. Meanwhile, functions of the antenna may be expanded, using the case. For example, the case having a conductive material is electrically connected with the antenna so that a grounded field or a radiated field can be expanded.

The display unit 351 may be disposed in a front surface of the main body 301 to display information. A touch sensor is provided in the display unit 351 so that the display unit 351 can be realized as a touch screen. As shown in the drawing, a window 351a of the display unit 351 is coupled to the first case 301a and the window may form a front surface of the terminal body, together with the first case 301a.

In the main body 301 may be provided an audio output unit 352, a camera 321, a microphone 322 and a user input unit 323. The display unit 351 realized as the touchscreen may be the user input unit 323 and no keys are provided in the main body 301.

The band 302 may be worn on the user's wrist to surround the wrist. The band 302 may be formed of a flexible material to facilitate the wearing. Examples of the flexible material used in the band 302 may include leather, rubber, silicon and synthetic resin. In addition, the band 302 is detachably coupled to the main body 301, so that the user may change diverse types of bands according to personal taste.

Meanwhile, the band 302 may be used in expand the functions of the antenna. For example, a ground expansion portion (not shown) for expanding the grounded field may be loaded in the band and the ground expansion portion is electrically connected with the antenna.

The band 302 may include a fastener 302a. The fastener 302a may be realized by a buckle, a snap-fit hook or Velcro. The band 302 may include a retractile section or material. In the drawing, the fastener 302a is realized as a buckle.

FIG. 18 is a diagram illustrating synchronization between the mobile terminal 100 and the wearable device 200 in accordance with the present disclosure. The user often leave the mobile terminal 100 in a bathroom or forgets the mobile terminal 100 put in a place. When the wearable device 200 and the mobile terminal 100 are getting distant from each other, it is difficult to monitor the wearable device 200, using the mobile terminal 100. However, the watch type mobile terminal 300 is carried continuously, unless the user takes off the watch type mobile terminal 300 on purpose after wearing. When using the watch type mobile terminal 300 and the mobile terminal 100 simultaneously, the wearable device 200 may be used more precisely.

To synchronize the mobile terminal 100 with the wearable device 200, the mobile terminal 100 or the watch type mobile terminal 300 senses a wearable device 200 which can perform short range wireless communication, when a wearable device 200 approaches in a preset range. The mobile terminal 100 or the watch type mobile terminal 300 may check synchronization with the wearable device 200 or require a unique number of the wearable device 300.

A shoe or a shoe insole type wearable device 200 may be in a short range wireless communicable distance and automatically synchronized, in case the user is using the mobile terminal 100 or wearing the watch type mobile terminal 300.

At this time, the wearable device 200 may transmit data about the number of times the pressure sensing unit 200 sensing the pressure or practicing the acupressure treatment or information about battery remains to the mobile terminal 100 or the watch type mobile terminal 300.

In addition, the mobile terminal 100 and the watch type mobile terminal 300 controls a sensitivity degree of the pressure sensing of the wearable device 200 or control the acupressure unit 230 of the wearable device 200 to practice acupressure for a specific area.

Figure 19:
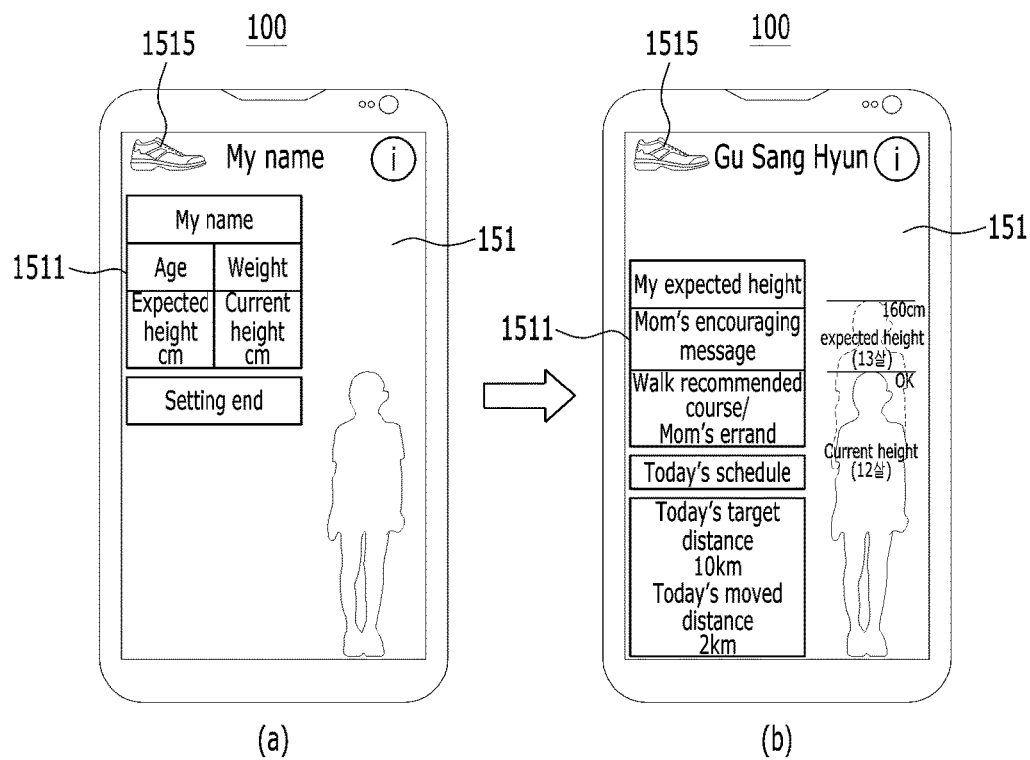

FIGS. 19 through 21 are diagrams illustrating setting of a height growth application, using the mobile terminal 100 in accordance with the present disclosure. When the wearable device 200 and the mobile terminal 100 are synchronized with each other, a corresponding program may be activated. The wearable device user's name, age, weight, current height and the like are input and a basic setting 1511 may be performed. Rather than that, the user's parent height, past growth record, ingested nutrient and the like may be further input.

Figure 20A:
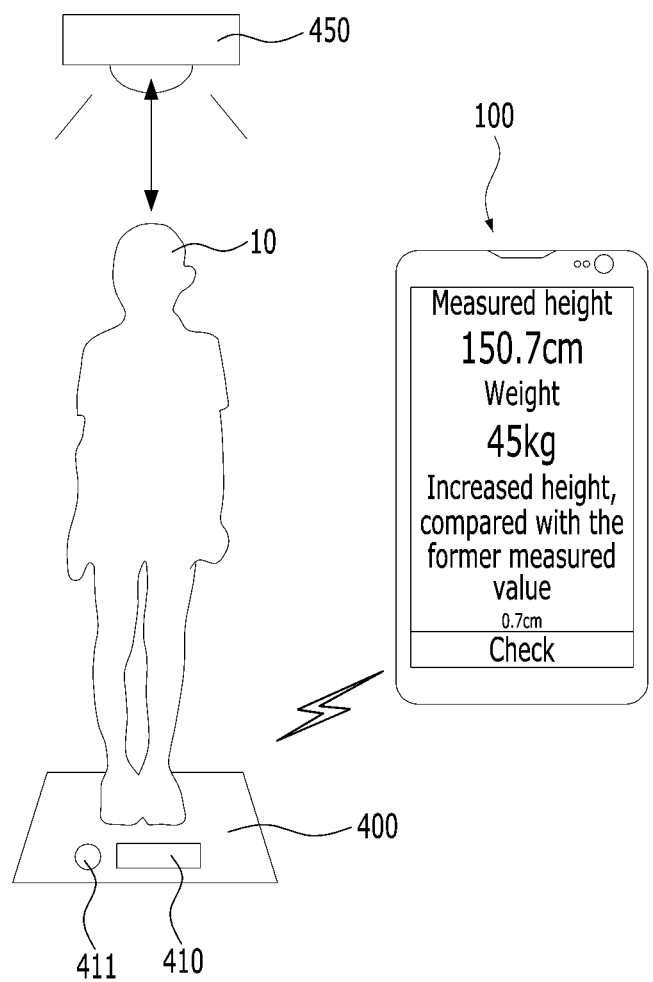

The user's current height and weight may be measured, using the wireless charger 400 mentioned above. As shown in FIG. 20a, the user wearing the wearable device 200 is standing on the wireless charger 400 and the user's current height and weight are automatically measured. The measured height and weight may be transmitted to the mobile terminal 100. After measuring the weight and current height, the mobile terminal 100 notifies the user that the measurement is ended, using an alarm function of the wireless charger 400.

Figure 20B:
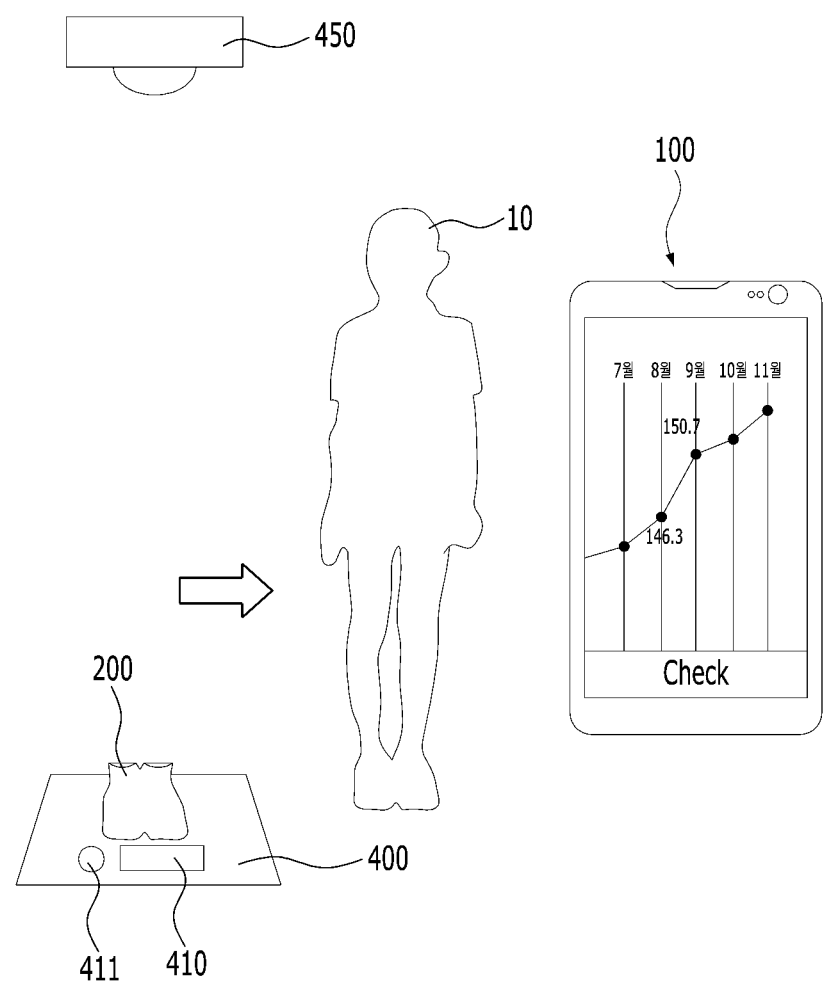

Once the measurement is ended as shown in FIG. 20b, the mobile terminal 100 may show cumulating data, using graphs, and the mobile terminal 100 may provide an alarm so measure the user's height and weight periodically so as to record the user's height and weight.

After the measurement, the mobile terminal 100 or the wireless charger 400 may guide the user puts the wearable device 200 on the wireless charger 400 and then steps down from the wireless charger 400.

The wireless charger 400 determines that only the wearable device 200 is put thereon, when the left weight is corresponding to the weight of the wearable device 200, and the wireless charger 400 starts electric power transmission after that. The wearable device 200 may transmit the charging amount to the user's mobile terminal 100, so that the user can check charging completion.

In case the charging is not completed, with no pressure applied to the pressure sensing unit 220, it is determined that the user takes off and puts the wearable device 200 in another place, not on the wireless charger 400. In this instance, the mobile terminal 100 (or the watch type mobile terminal) warns the user to put the wearable device 200 on the wireless charger 400.

As shown in FIG. 21 (*a*), a one-day target distance and a target data are input to calculate an expected height on the target date based on the weight and current height. In case the user walks as far as one-day target distance until the target date, the growth may be calculated based on the number of times practicing growing point acupressure treatment. The precise expected height may be calculated based on the user's parents height, past growth record and ingested nutrient rather than the user's weight and height.

As shown in FIG. 21 (*b*), in case there is a much difference or more between one-day average walking distance and one-day target distance once the user fails to achieve one-day target distance for preset time period, the expected height may be changed. In case height determination factors, for example, the height and the weight are changed, the expected height may be adjusted a little bit.

A guide message for measuring the user's height periodically may be output at stated periods. When the user is not wearing the wearable device 200, with not charging the wearable device 200, an alarm message may be output to notify the user of putting the wearable device 200 on the wireless charger 400.

Figure 22:
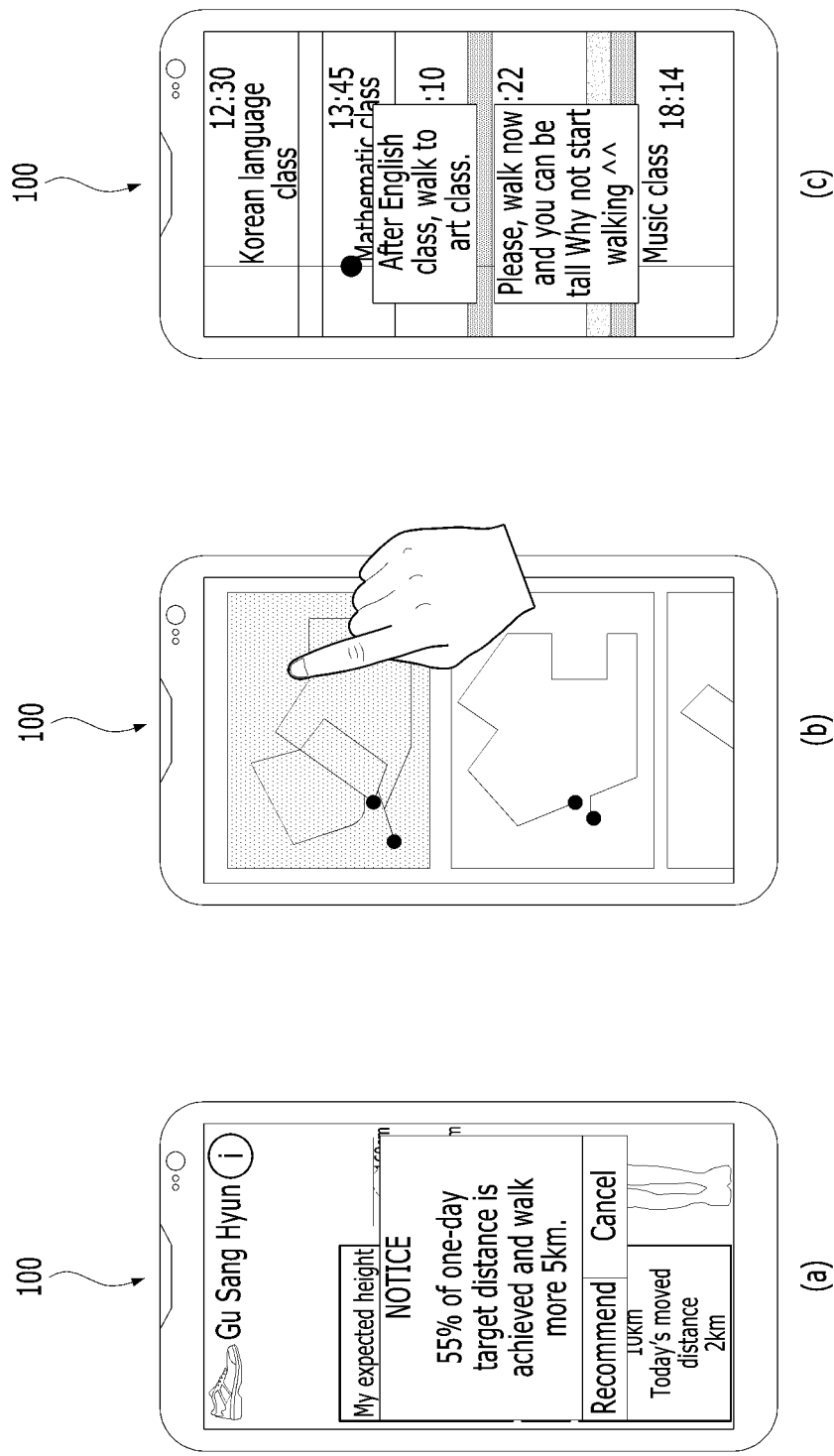
FIG. 22 is a diagram illustrating a function for assisting a user to achieve an one-day target distance of the mobile terminal in accordance with the present disclosure.

FIG. 22 is a diagram illustrating a function for assisting a user to achieve a one-day target distance of the mobile terminal in accordance with the present disclosure. in case the user fails to achieve a selected one-day target distance at a specified time (for example, four o'clock in the afternoon not even close to a preset level or less (for example, 60%) as shown in FIG. 22 (*a*), the user may be required to walk more.

The mobile terminal may recommend a walking course as shown in FIG. (b) and guide the user to make the targeted number of walking. When selecting a preferred walking course, the user is guided to walk along the selected walking course and description about a building located in the walking course may be provided to arouse the user's interest.

In case the user's schedule is registered on the mobile terminal 100, a recommended course may be configured based on the registered schedule as shown in FIG. 22 (*c*). The user is induced to walk for the next schedule and a message of support may be provided.

Figure 23:
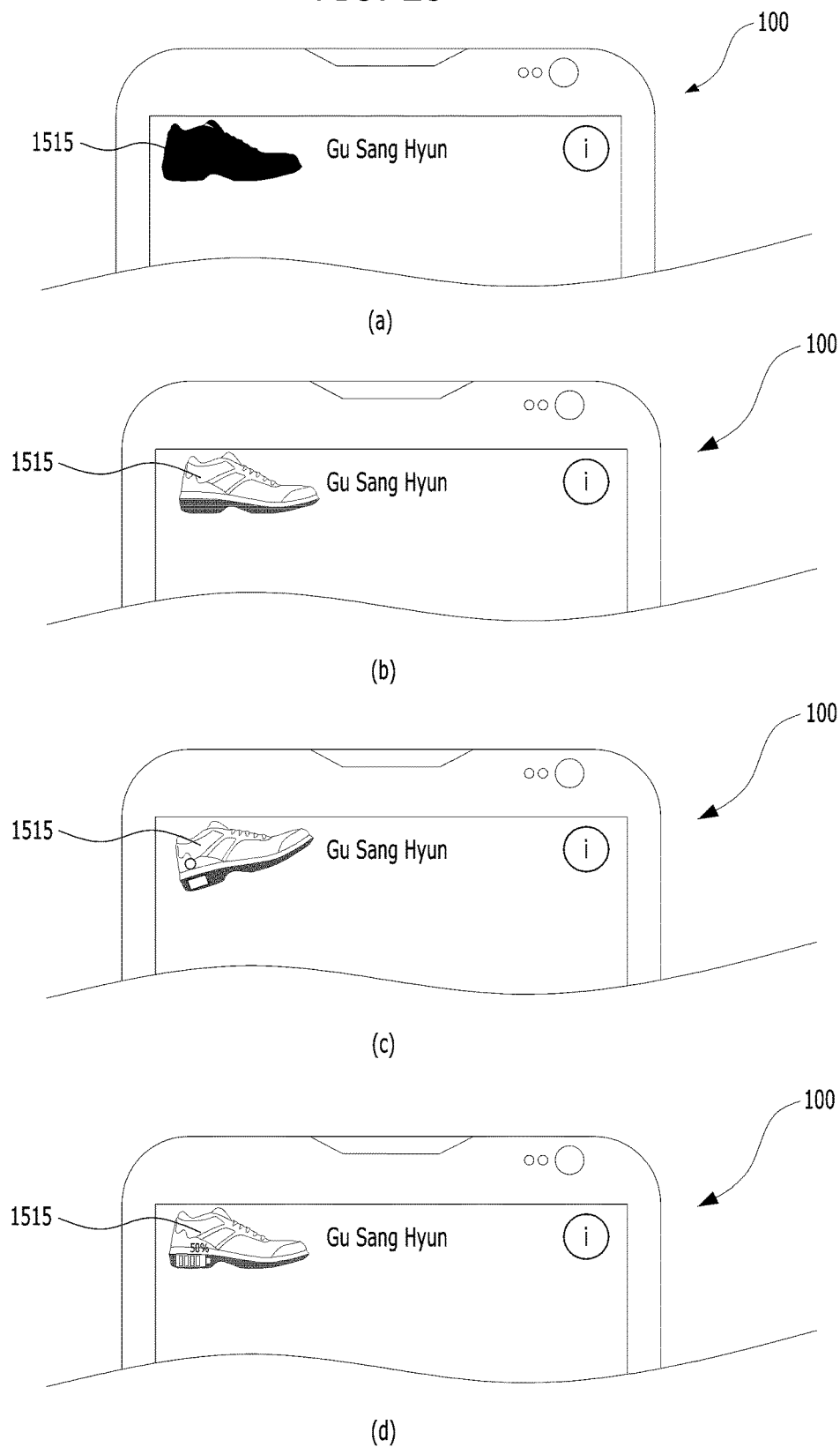
FIG. 23 is a diagram illustrating an indicator displayed on a display unit of the mobile terminal in accordance with the present disclosure.

FIG. 23 is a diagram illustrating an indicator displaying a status of the wearable device 200 on a display unit of the mobile terminal 100 in accordance with the present disclosure. The indicator indicates a status of the wearable device 200. After the synchronization, a color is changed or an image is changed as shown in (b) from a dark color shown in (a) in a state where the wearable device is not synchronized with the mobile terminal 100.

Once the user starts to walk, points at which the pressure sensing unit 220 senses the pressure may be displayed and points at which the acupressure unit 230 practices acupressure treatment may be displayed and it is displayed the number of times pressing acupressure point is accumulating. Hence, when the user puts the wearable device 200 on the wireless charger 400, the wearable device 200 starts to be charged and an indicator for indicating a state of charge may be displayed.

When the wearable device 200 is not charged, with the user not wearing the wearable device 200, an auxiliary pop-up is displayed to induce the charge of the wearable device 200. However, using the indicator, it may be displayed that charge is required.

Figure 24:
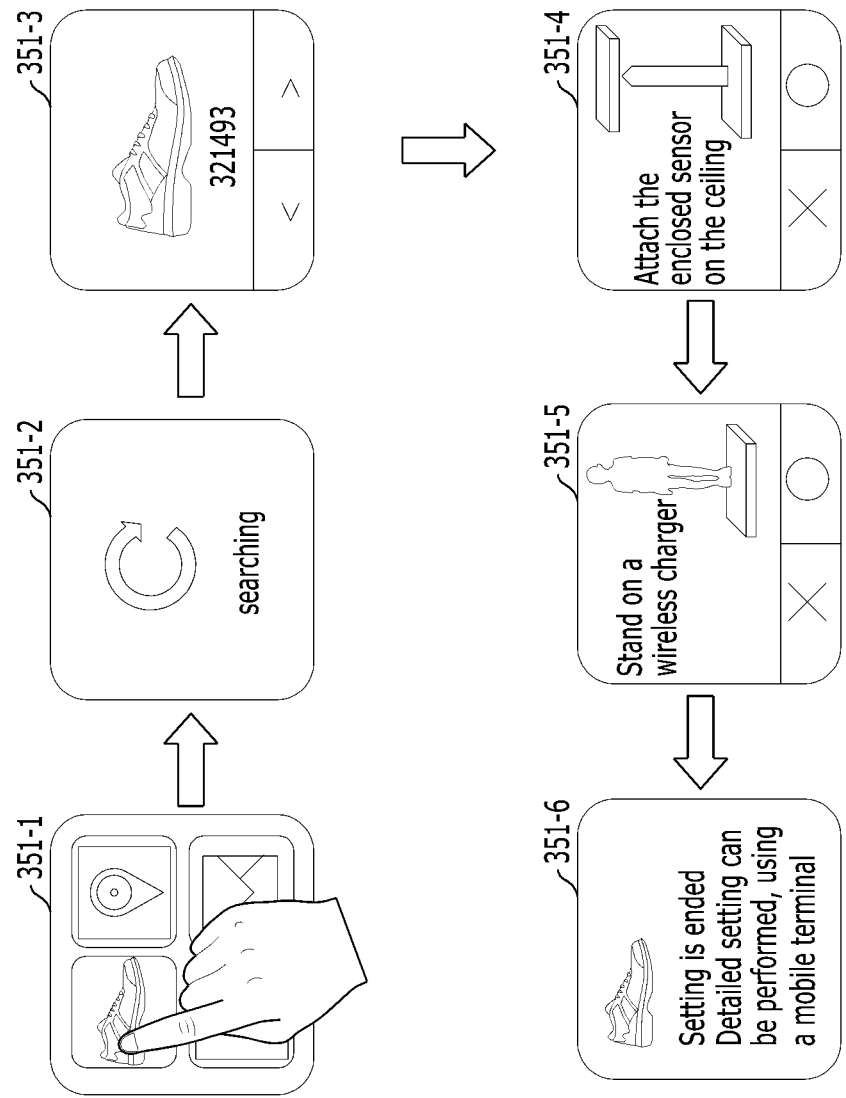
FIG. 24 is a diagram illustrating a method for initially setting the wearable device and a watch type mobile terminal in accordance with the present disclosure.

FIG. 24 is a diagram illustrating a method for initially setting the wearable device and a watch type mobile terminal in accordance with the present disclosure. When the wearable device 200 and the watch type mobile terminal 300 are within a preset distance after the setting, synchronization is automatically performed between the wearable device 200 and the watch type mobile terminal 300.

When the user activates a control function of the wearable device 200 (351-1), presence of the wearable device 200 in the preset distance is automatically checked, using the wireless communication unit. The searched wearable device 200 is displayed on the display unit. When recognizing the searched wearable device 200, the user is guided to measure and input the height and weight, using the wireless charger 400 (351-4 and 351-5). Once the initial setting is completed, the user is notified that the setting is completed (S351-6).

Figure 25:
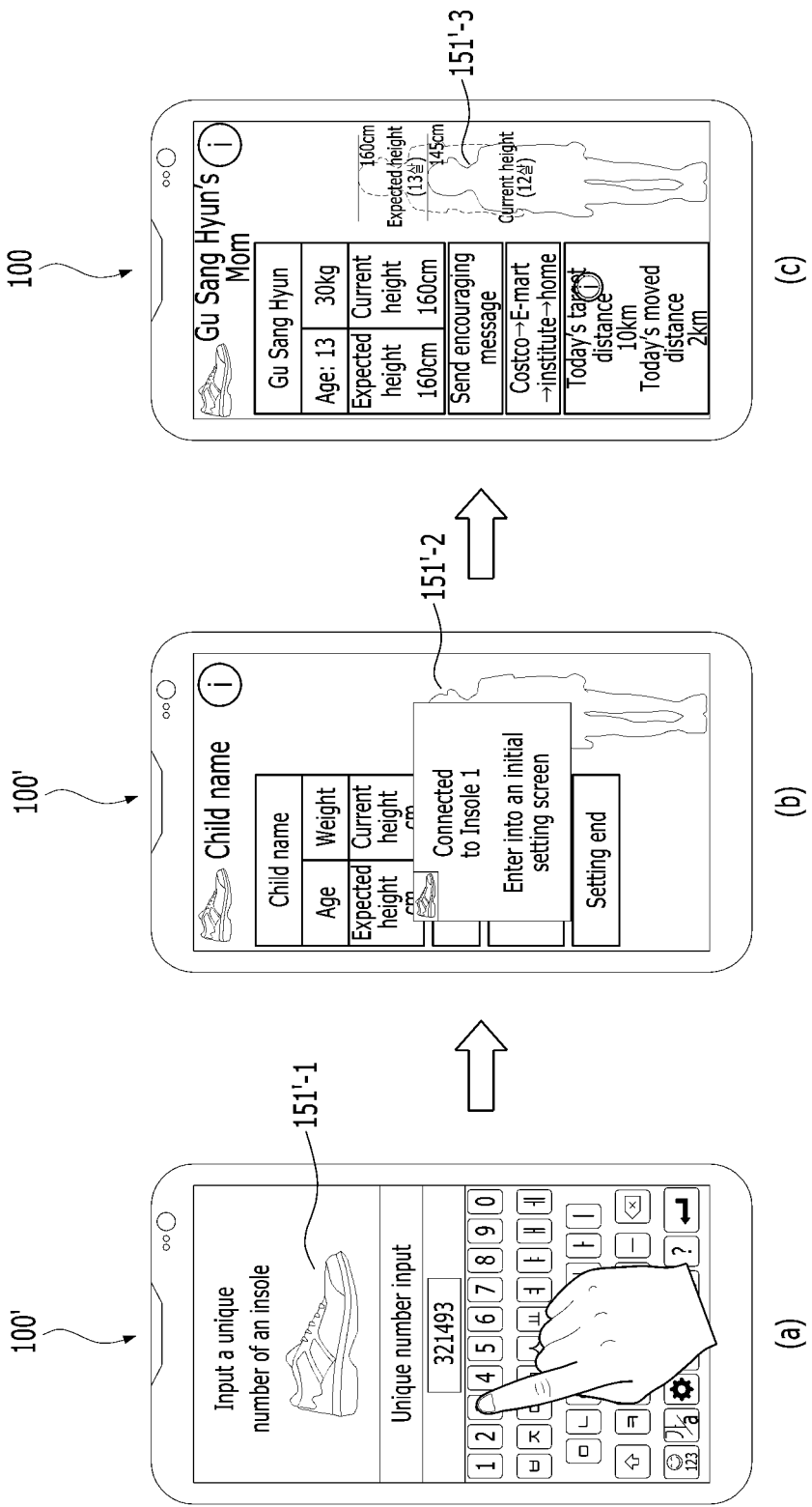
FIG. 25 is a diagram illustrating a method for permitting a third person, not the user of the wearable device in accordance with the present disclosure to register the wearable device.

FIG. 25 is a diagram illustrating a method for permitting a third person, not the user of the wearable device in accordance with the present disclosure to register the wearable device. The third person may manage the user's growth. For example, the third person may be the user's mother.

The mother's mobile terminal 100' may exchange data with the child's mobile terminal 100 or the watch type mobile terminal. In case it performs only the short range wireless communication, the wearable device 200 may not perform wireless communication via a telecommunication company and the wearable device 200 may not be directly synchronized with the mother's mobile terminal 100' distant a long distance. Accordingly, the child's mobile terminal 100 and the mother's mobile terminal 100' may exchange data via a base station.

To initially connect the mobile terminals with each other, a unique number of the wearable device 200, for example, (151'-1) is input even without the wearable device 200 located nearby and a function for managing the wearable device 200 may be usable. Once the unique number of the wearable device 200 is input, the user's mobile terminal 100 or the watch type mobile terminal 300 connected with the corresponding wearable device 200 may wirelessly communicate with the wearable device 200 or receive information on the wearable device 200 via a server (151'-2). In case corresponding information is insufficient, insufficient information may be input from the mother's mobile terminal 100' additionally (151-3).

Figure 26:
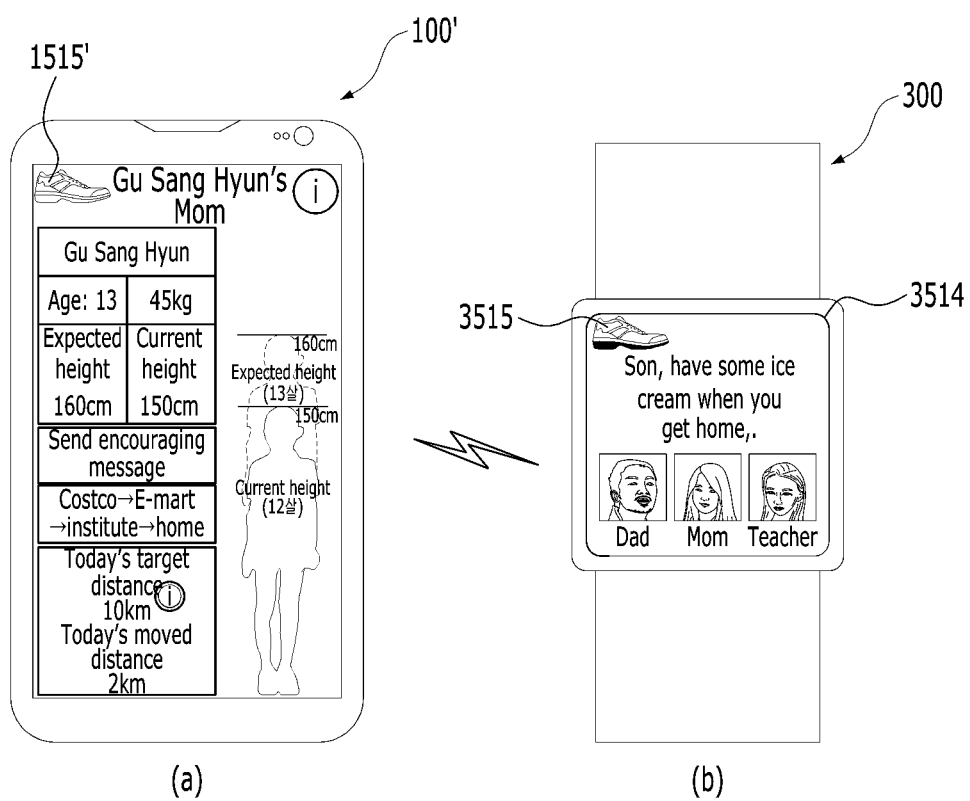
FIG. 26 is a diagram illustrating one embodiment of a method for permitting a third person, not the user of the wearable device in accordance with the present disclosure, to check the data collected in the wearable device.

FIG. 26 is a diagram illustrating one embodiment of a method for permitting a third person, not the user of the wearable device 200 in accordance with the present disclosure, to check the data collected in the wearable device 200.

At this time, the child's mobile terminal 100 synchronized with the wearable device 200 is the watch type mobile terminal. The watch type mobile terminal 300 has a small-sized screen and detailed description is not displayed on the screen. Only a status of the wearable device 200 and an achieved distance with respect to one-day target distance may be displayed as an image.

As shown in FIG. 26, a closed-curve-shaped status display image 3514 is displayed along an outer portion of the display unit and the closed curve image shows a one-day target distance. As the user is walking, an area having a changed color is gradually increasing in the status display image 3514 and an entire color is changed in the entire area of the status display image, so that it is displayed that the target distance is achieved.

Figure 27:
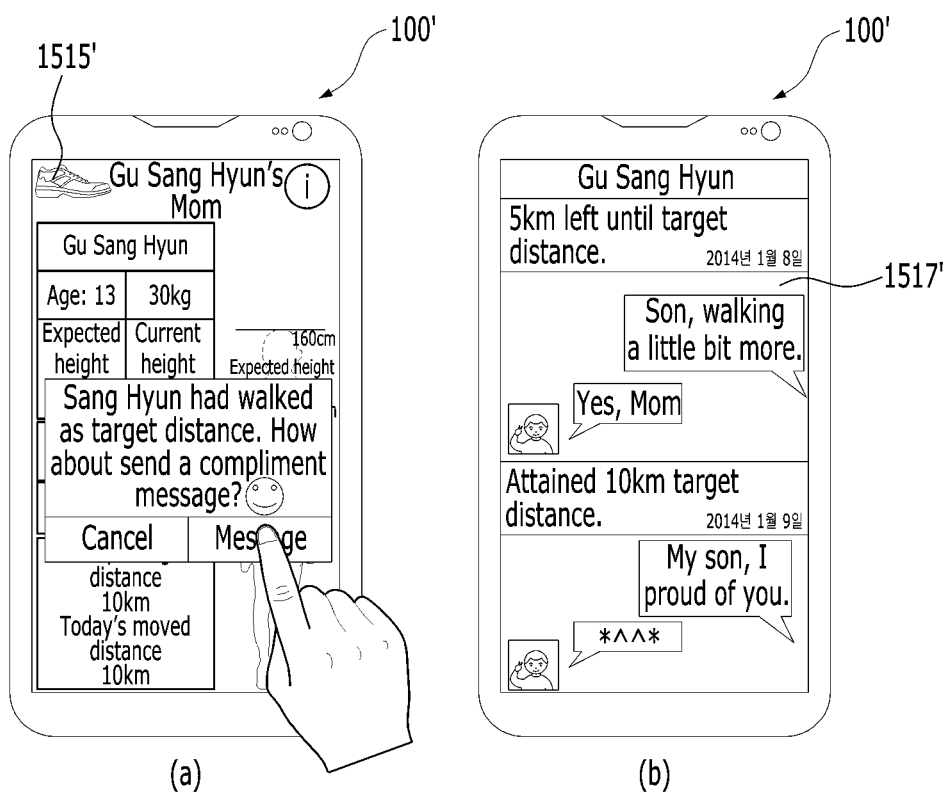
FIG. 27 is a diagram illustrating communication between the user's mobile terminal and a third person's mobile terminal.

FIG. 27 is a diagram illustrating communication between the user's mobile terminal and a third person's mobile terminal. The mother's mobile terminal 100' may receive information on a status of the wearable device 200 and the presence of the child's one-day target achievement and feedbacks thereon from the child's mobile terminal 100. For example, when information on the child's achievement of the target distance is transmitted to the mother's mobile terminal, the mother may send a message for rewarding the achievement to the child. If information on the child's failure of the one-day target distance is transmitted to the mother's mobile terminal, the mother may send a message for encouraging the child. Also, in case the expected height is short of the actual height, an additional plan for promoting the growth may be guided or visit to a hospital may be induced.

Figure 28:
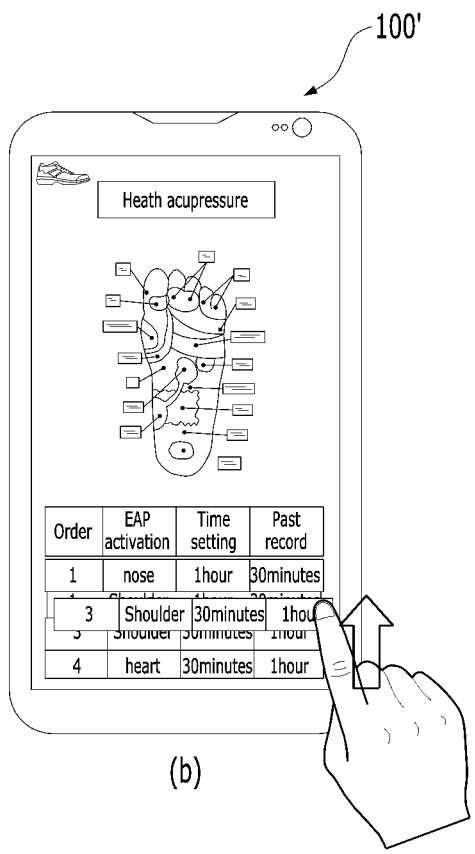
FIG. 28 is a diagram illustrating a method for controlling a plurality of acupressure units provided in the wearable device shown in FIG. 8.

FIG. 28 is a diagram illustrating a method for controlling a plurality of acupressure units provided in the wearable device 200 shown in FIG. 8. The mobile terminal 100 in accordance with the present disclosure may be used so as to practice acupressure treatment for the user's foot. Each of body parts is associated with the user foot location. When acupressure points of the sole associated with weak body organs are pressured, weak organs may be improved. The user may control the acupressure units corresponding to specific points to be projected in the wearable device 200, using the mobile terminal 100.

For user convenience, when the user selects a weak body part on the wearable device 200, acupressure points of the sole of the foot corresponding to the selected body part may be automatically pressed and the user may set the time of acupressure point pressing and the order of pressing acupressure points for body parts.

FIG. 28 shows the mobile terminal 100 for selecting and controlling the body parts to be improved. However, regardless of that, only the acupressure unit 230 corresponding to a specific point of the sole may be selected and controlled to be projected so as to press a corresponding acupressure point.

As mentioned above, in accordance with the embodiments of the present disclosure, the wearable device having the acupressure function is used and the user is guided to promote the growth and to relieve the stress.

Furthermore, the user may check the status of the wearable device, using the mobile terminal. Accordingly, the wearable device may be controlled conveniently and easily and usage of the wearable device may be enhanced.

The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A wearable device comprising:
a shoe;
a base provided in an insole of the shoe;
a plurality of pressure sensing units provided in the base to sense pressure;
a plurality of acupressure units including an acupressure projection to apply an acupressure to a user's foot, each of the plurality of acupressure units associated with a corresponding one of the pressure sensing units;
a control unit configured to control the plurality of acupressure units such that the acupressure projections are selectively controlled based on the pressure sensed by the corresponding pressure sensing units; and
a wireless communication unit synchronizable with an external mobile terminal.

2. The wearable device of claim 1, further comprising:
a battery to supply electric power; and
a wireless charging coil provided in the base to charge the battery when placed in an external electromagnetic field.

3. The wearable device of claim 1, wherein a plurality of acupressure modules are defined by the acupressure units and corresponding pressure sensing units,
wherein the control unit is configured to control at least one of the acupressure modules such that the acupressure projection is projected, when order of the pressure variation sensed by the pressure sensing unit is different from a preset order of pressure variation, and
wherein the acupressure modules are arranged along a longitudinal direction of the base.

4. The wearable device of claim 1, further comprising a battery to supply electric power to the acupressure units,
wherein each of the acupressure units is an electroactive polymer having a variable profile when a voltage is applied thereto, and
wherein the control unit is configured to:
apply a first-leveled voltage corresponding to a first height variation of the acupressure unit to the acupressure unit,
measure a second height variation of the acupressure unit based on pressure variation sensed by the pressure sensing unit, and
calculate a compensated voltage having a level corresponding to a difference between the first height variation and the second height variation, when the first height variation is different from the second height variation, and
apply a pressure corresponding to the compensated voltage to the acupressure unit.

5. A wireless charger comprising:
a wireless charging panel configured to measure the weight of a user standing on a top surface thereof, the wireless charger comprising a wireless electric power transmission coil;
a height measuring sensor provided on a structure vertically over the wireless charging panel to measure a current height of the user when the user is standing on the wireless charging panel; and
a wireless communication unit configured to transmit data of the user's current height measured by the height measuring sensor and the weight measured by the wireless charging panel to an external mobile terminal.

6. The wireless charger of claim 5, wherein the wireless communication unit is synchronized with a wearable device configured to perform an acupressure function for practicing acupressure treatment on a foot of the user; and wherein the wireless charger further comprises a user input unit configured to receive an input of a walking target distance for the user.

7. A mobile terminal comprising:
a height input unit configured to receive a current height of a user;
a wireless communication unit synchronized with a wearable device configured to perform an acupressure function for practicing acupressure treatment on a foot of the user;
a user input unit configured to receive an input of a target walking distance and a target walking time; and
a control unit configured to calculate an expected height based on the user's current height, the target walking distance and the target walking time.

8. The mobile terminal of claim 7, further comprising a GPS module configured to receive location information of the mobile terminal,
wherein the control unit calculates a moved distance of the user based on a change of location information received by the GPS module, and
wherein, when there is a difference between the user's moved distance and a one-day target of the target walking distance, the control unit corrects the expected height.

9. The mobile terminal of claim 7, wherein the control unit adjusts the expected height when the current height is updated.

10. The mobile terminal of claim 7, wherein the wearable device includes an acupressure unit configured to apply a pressure to a lateral surface of an ankle of the user and a curvature measurer provided to sense curvature variation generated when the user is walking, and
the control unit calculates a precise position of an ankle bone of the user based on the curvature variation measured by the curvature measurer and controls the wireless communication unit to transmit a command for controlling a position of the acupressure unit provided in the wearable device.

11. The mobile terminal of claim 7, wherein a step of the user is calculated based on the user's current height and the target distance is calculated as a step count based on the user's step, and
the expected height is calculated based on the step count.

12. The mobile terminal of claim 7, wherein the control unit controls an indicator to be output on a display unit of the mobile terminal to indicate a status of the wearable device, and
wherein the status of the wearable device includes one of walking, charging, low battery remaining and synchronization checking.

13. The mobile terminal of claim 7, wherein the control unit is configured to provide an alarm notifying the user of failure of a one-day target distance, using an external mobile terminal, when a one-day moved distance fails to reach the one-day target distance of the target walking distance.

* * * * *